US012767480B2

(12) United States Patent
Kim et al.

(10) Patent No.: US 12,767,480 B2
(45) Date of Patent: Oct. 20, 2026

(54) TUBULAR MEMBER MOVING APPARATUS

(71) Applicant: Endo Robotics Co., Ltd., Seoul (KR)

(72) Inventors: Byung Gon Kim, Seoul (KR); Kyungnam Kim, Seoul (KR); Yechan Seo, Seoul (KR); Taebin Kwon, Seoul (KR); Yongsik Kwon, Seoul (KR)

(73) Assignee: EndoRobotics Co., Ltd., Seoul (KR)

( * ) Notice: Subject to any disclaimer, the term of this patent is extended or adjusted under 35 U.S.C. 154(b) by 678 days.

(21) Appl. No.: 17/804,400

(22) Filed: May 27, 2022

(65) Prior Publication Data

US 2022/0380169 A1 Dec. 1, 2022

(30) Foreign Application Priority Data

May 28, 2021 (KR) ........................ 10-2021-0068997
Mar. 18, 2022 (KR) ........................ 10-2022-0034302

(51) Int. Cl.
*B65H 51/10* (2006.01)
*A61B 1/00* (2006.01)
*B65H 57/00* (2006.01)

(52) U.S. Cl.
CPC ............ *B65H 51/10* (2013.01); *A61B 1/0016* (2013.01); *B65H 57/00* (2013.01); *B65H 2404/1441* (2013.01); *B65H 2551/15* (2013.01)

(58) Field of Classification Search
CPC ............ B65H 51/10; B65H 2404/1441; B65H 2551/15; A61B 1/0133; A61B 1/0016;
(Continued)

(56) References Cited

U.S. PATENT DOCUMENTS 2,272,158 A * 2/1942 Anderson .............. B65H 51/10
74/25
2,670,926 A * 3/1954 Sewell ..................... G01V 1/20
226/186
(Continued)

FOREIGN PATENT DOCUMENTS

JP H01-148232 A 6/1989
JP H09-108180 A 4/1997
(Continued)

OTHER PUBLICATIONS

Office Action of the corresponding Japanese Application No. 2022-087132, dated May 23, 2023.
(Continued)

*Primary Examiner* — Erin M Piateski
*Assistant Examiner* — Katelynne R Burrell
(74) *Attorney, Agent, or Firm* — Knobbe, Martens, Olson & Bear, LLP

(57) ABSTRACT

Provided is a tubular member moving apparatus. A tubular member moving apparatus is configured to move a tubular member and includes a first housing through which the tubular member passes, a driving roller unit including a driving roller provided in the first housing and disposed at one side of the tubular member, a driven roller unit including a first driven roller disposed at the other side of the tubular member, a first actuator configured to provide driving power for rotating the driving roller, and a second housing separably coupled to the first housing and configured to accommodate the first actuator therein.

9 Claims, 19 Drawing Sheets

160 : 161, 162, 163, 164, 165, 166, 168, 169

(58) Field of Classification Search
CPC ... A61B 1/00131; A61B 1/00133; A61B 1/00; A61M 25/0113
See application file for complete search history.

(56) References Cited

U.S. PATENT DOCUMENTS

| | | | | |
|---|---|---|---|---|
| 3,835,854 | A * | 9/1974 | Jewett | A61M 25/0113 604/159 |
| 3,964,657 | A * | 6/1976 | Lenk | B65H 51/16 226/177 |
| 5,346,498 | A * | 9/1994 | Greelis | A61M 25/0119 606/108 |
| 5,709,661 | A | 1/1998 | Van Egmond et al. | |
| 6,290,675 | B1 * | 9/2001 | Vujanic | A61M 25/0113 604/164.13 |
| 6,398,755 | B1 * | 6/2002 | Belef | A61M 25/0113 604/95.01 |
| 6,569,086 | B2 * | 5/2003 | Motoki | A61B 1/0016 600/151 |
| 6,752,758 | B2 * | 6/2004 | Motoki | A61B 1/0016 600/104 |
| 7,041,053 | B2 * | 5/2006 | Miyake | A61B 1/0016 600/152 |
| 8,449,455 | B2 * | 5/2013 | Honda | A61B 1/00016 340/3.1 |
| 9,782,564 | B2 * | 10/2017 | Zirps | A61M 25/0116 |
| 10,668,552 | B2 * | 6/2020 | Fujii | B23K 9/133 |
| 12,214,552 | B2 * | 2/2025 | Bondéus | B33Y 10/00 |
| 12,369,775 | B2 * | 7/2025 | Nord | A61B 1/00133 |
| 2002/0022765 | A1 * | 2/2002 | Belson | A61B 1/31 600/146 |
| 2006/0146010 | A1 * | 7/2006 | Schneider | A61M 25/0113 345/156 |
| 2007/0021695 | A1 | 1/2007 | Wu | |
| 2008/0262296 | A1 | 10/2008 | Suzuki | |
| 2009/0013808 | A1 | 1/2009 | Ehrenberg | |
| 2010/0234873 | A1 * | 9/2010 | Nagano | G01L 5/0038 254/133 R |
| 2010/0305502 | A1 * | 12/2010 | Ferry | A61B 90/50 604/95.01 |
| 2011/0208000 | A1 * | 8/2011 | Honda | A61B 1/0016 600/118 |
| 2011/0221126 | A1 * | 9/2011 | Ohkubo | G03G 15/2032 271/272 |
| 2012/0035596 | A1 * | 2/2012 | Tegg | A61M 25/0113 606/1 |
| 2012/0271105 | A1 * | 10/2012 | Nakamura | A61B 1/31 600/114 |
| 2014/0277333 | A1 * | 9/2014 | Lewis | A61B 34/30 623/1.11 |
| 2014/0296633 | A1 * | 10/2014 | Gumbs | A61B 1/0057 600/109 |
| 2017/0225919 | A1 * | 8/2017 | Takanami | H05K 13/0419 |
| 2018/0001413 | A1 * | 1/2018 | Fujii | B23K 9/173 |
| 2019/0152737 | A1 * | 5/2019 | Hunt | B65H 57/14 |
| 2020/0038106 | A1 * | 2/2020 | Pieper | A61B 34/30 |
| 2020/0297434 | A1 | 9/2020 | Bencteux et al. | |
| 2021/0000578 | A1 * | 1/2021 | Jackson | A61C 15/047 |
| 2021/0045823 | A1 | 2/2021 | Landey et al. | |
| 2022/0163140 | A1 * | 5/2022 | Cheng | B65H 51/10 |
| 2022/0354341 | A1 * | 11/2022 | Chen | A61B 1/00124 |
| 2023/0294954 | A1 * | 9/2023 | Kim | A61B 34/30 226/24 |
| 2024/0023990 | A1 * | 1/2024 | Braun | A61B 17/3423 |
| 2024/0206905 | A1 * | 6/2024 | Menn | A61B 34/30 |
| 2025/0171267 | A1 * | 5/2025 | Bondéus | B65H 51/10 |

FOREIGN PATENT DOCUMENTS

| | | | | |
|---|---|---|---|---|
| JP | H09-140663 | A | 6/1997 | |
| JP | 2008-154758 | A | 7/2008 | |
| JP | 2009-055956 | A | 3/2009 | |
| WO | WO-2016114186 | A1 * | 7/2016 | B23K 9/124 |
| WO | WO 2021/049944 | A1 | 3/2021 | |

OTHER PUBLICATIONS

Office Action from European Application No. 22175729.7 dated Oct. 10, 2022.

* cited by examiner (a)

(b)

(a)

(b)

160 : 161, 162, 163, 164, 165, 166, 168, 169

160 : 161, 162, 163, 164, 165, 166, 168, 169

160 : 161, 162, 163, 164, 165, 166, 168', 169'

TUBULAR MEMBER MOVING APPARATUS

CROSS REFERENCE TO RELATED APPLICATION

The present application claims priority to Korean Patent Application No. 10-2021-0068997, filed May 28, 2021 and Korean Patent Application No. 10-2022-0034302, filed Mar. 18, 2022, the entire contents of which are incorporated herein by reference.

BACKGROUND

Field

The present disclosure relates to a tubular member moving apparatus, and more particularly, to a tubular member moving apparatus capable of moving a tubular member.

Description of the Related Art

An endoscope refers to a device implemented to be inserted into a body and used to check a lesion in an organ that cannot be directly observed without performing a surgical procedure or autopsy. Recently, various types of surgical instruments have been devised to perform a procedure on the interior of the organ without incising a patient's body.

A part of an endoscopic device, which is inserted into the human body, is generally provided in the form of a tubular member to conform to structural features of the body and minimize an area of a surgical site. For example, there has been developed an apparatus for inserting the endoscope attached with surgical instruments into the patient's body and performing a surgical procedure.

In addition, the tubular member is widely used for apparatuses for checking and inspecting interiors of structures or pipes to ensure convenience and efficiency in inserting and extracting the tubular member.

In the industrial and medical sites, the tubular member is repeatedly inserted and extracted during a working process. To this end, significant amounts of time and labor are required. There has been developed a moving apparatus configured to automatically insert or extract the tubular member in order to reduce the amounts of time and labor required to insert and extract the tubular member.

The moving apparatus includes a structure in which a driving roller configured to rotate by receiving driving power from a motor and a driven roller configured to freely rotate are disposed to adjoin two opposite portions of the tubular member. The tubular member is moved by a frictional force generated between the driving roller and the tubular member.

The disclosure of this section is to provide background information relating to the present disclosure. Applicant does not admit that any information contained in this section constitutes prior art.

SUMMARY

In an example of a moving apparatus, an area in which the tubular member and the driving roller are in contact with each other is not sufficient, the driving power generated by the motor cannot be efficiently transmitted to the tubular member.

In addition, in the moving apparatus, the entire moving apparatus needs to be cleaned or replaced when the interior of the moving apparatus is contaminated by the tubular member, the electronic components such as the motor are damaged during the cleaning process, and reusable components are discarded, which wastes resources.

The present disclosure aims to provide a tubular member moving apparatus capable of automatically inserting or extracting a tubular member.

The present disclosure also aims to provide a tubular member moving apparatus capable of easily switching a mode from an automatic mode in which a tubular member is automatically inserted or extracted to a manual mode in which the tubular member is manually inserted or extracted or vice versa.

The present disclosure also aims to provide a tubular member moving apparatus capable of efficiently moving a tubular member by increasing a contact area between a driving roller and a tubular member.

The present disclosure also aims to provide a tubular member moving apparatus capable of separating and cleaning only a component contaminated by a tubular member.

An aspect of the present disclosure provides a tubular member moving apparatus, which is configured to move a tubular member, the tubular member moving apparatus including: a first housing through which the tubular member passes; a driving roller unit including a driving roller provided in the first housing and disposed at one side of the tubular member; a driven roller unit including a first driven roller disposed at the other side of the tubular member; a first actuator configured to provide driving power for rotating the driving roller; and a second housing separably coupled to the first housing and configured to accommodate the first actuator therein.

In this case, the tubular member moving apparatus may further include a roller operating unit configured to move the first driven roller to a first position from a second position farther from the driving roller than the first position adjacent to the driving roller.

In this case, the roller operating unit may include a second actuator configured to move the first driven roller from the second position to the first position, and the second actuator may be positioned in the second housing.

In this case, the second actuator may be a linear actuator, and the linear actuator may be connected to the first driven roller by means of a plurality of connection members.

In this case, the roller operating unit may include: a first link disposed in the first housing and having one side coupled to the first housing so as to be pivotally rotatable about a first axis; a second link coupled to the first link and the first driven roller; and a button member connected to the first link and installed in the first housing.

In this case, an elastic member may be provided on the button member and provide an elastic force so that the button member protrudes to the outside of the first housing and the first driven roller is spaced apart from the driving roller by an interval larger than a diameter of the tubular member in a state in which no external force is applied.

In this case, the roller operating unit may include an elastic member configured to elastically press the first driven roller in a direction from the second position to the first position.

In this case, the driven roller unit may include a second driven roller disposed to be spaced apart from the first driven roller in a longitudinal direction of the tubular member, and the driving roller may be positioned between the first and second driven rollers in the longitudinal direction of the tubular member.

In this case, the tubular member may be moved while being bent and having a predetermined curvature along an outer peripheral surface of the driving roller in the first housing.

In this case, a diameter of each of the first and second driven rollers may be smaller than a diameter of the driving roller.

In this case, a guide member may be provided in the first housing and guide the tubular member.

In this case, the tubular member may be disposed outside the second housing while penetrating the first housing.

In this case, the second housing may include an operating button configured to operate the first actuator.

According to the tubular member moving apparatus according to the embodiment of the present disclosure, the driving roller unit, which rotates by receiving driving power from the actuator, applies the frictional force in the movement direction of the tubular member, which makes it possible to automatically insert or extract the tubular member.

In addition, according to the tubular member moving apparatus according to the embodiment of the present disclosure, the roller operating unit may allow the driven roller to be positioned adjacent to the driving roller or allow the driven roller to be spaced apart from the driving roller, which makes it possible to easily switch the mode from the automatic mode to the manual mode or vice versa.

In addition, according to the tubular member moving apparatus according to the embodiment of the present disclosure, the driving roller and the actuator are disposed adjacent to each other, and the driven roller and the roller operating unit are disposed adjacent to each other. Therefore, the internal components are compactly disposed, a width of the tubular member moving apparatus in the forward/rearward direction is small, the tubular member moving apparatus is light in weight, and the tubular member moving apparatus is excellent in power transmission efficiency.

In addition, according to the tubular member moving apparatus according to the embodiment of the present disclosure, the second housing configured to accommodate the actuator is disposed to be opposite to the roller operating unit with respect to the tubular member, which makes it possible to improve convenience and efficiency for the user's manipulation.

In addition, according to the tubular member moving apparatus according to the embodiment of the present disclosure, the roller operating unit includes the elastic member configured to elastically press the driven roller toward the driving roller. Therefore, the driven roller may apply a predetermined force and press the tubular member regardless of a diameter of the tubular member.

In addition, according to the tubular member moving apparatus according to the embodiment of the present disclosure, the plurality of driven rollers presses the tubular member toward the driving roller, such that the tubular member surrounds the outer peripheral surface of the driving roller while being bent, which makes it possible to increase the contact area between the driving roller and the tubular member.

The effects of the present disclosure are not limited to the above-mentioned effects, and other effects, which are not mentioned above, may be clearly understood by those skilled in the art from the present specification and the accompanying drawings.

BRIEF DESCRIPTION OF THE DRAWINGS

FIGS. 14 and 15 are views for explaining operating processes of the tubular member moving apparatus according to the second embodiment of the present disclosure, in which FIG. 14 is a view illustrating a state (automatic mode) in which the driven roller is positioned at a first position, and FIG. 15 is a view illustrating a state (manual mode) in which the driven roller is positioned at a second position.

DETAILED DESCRIPTION OF EMBODIMENTS

Figure 1:
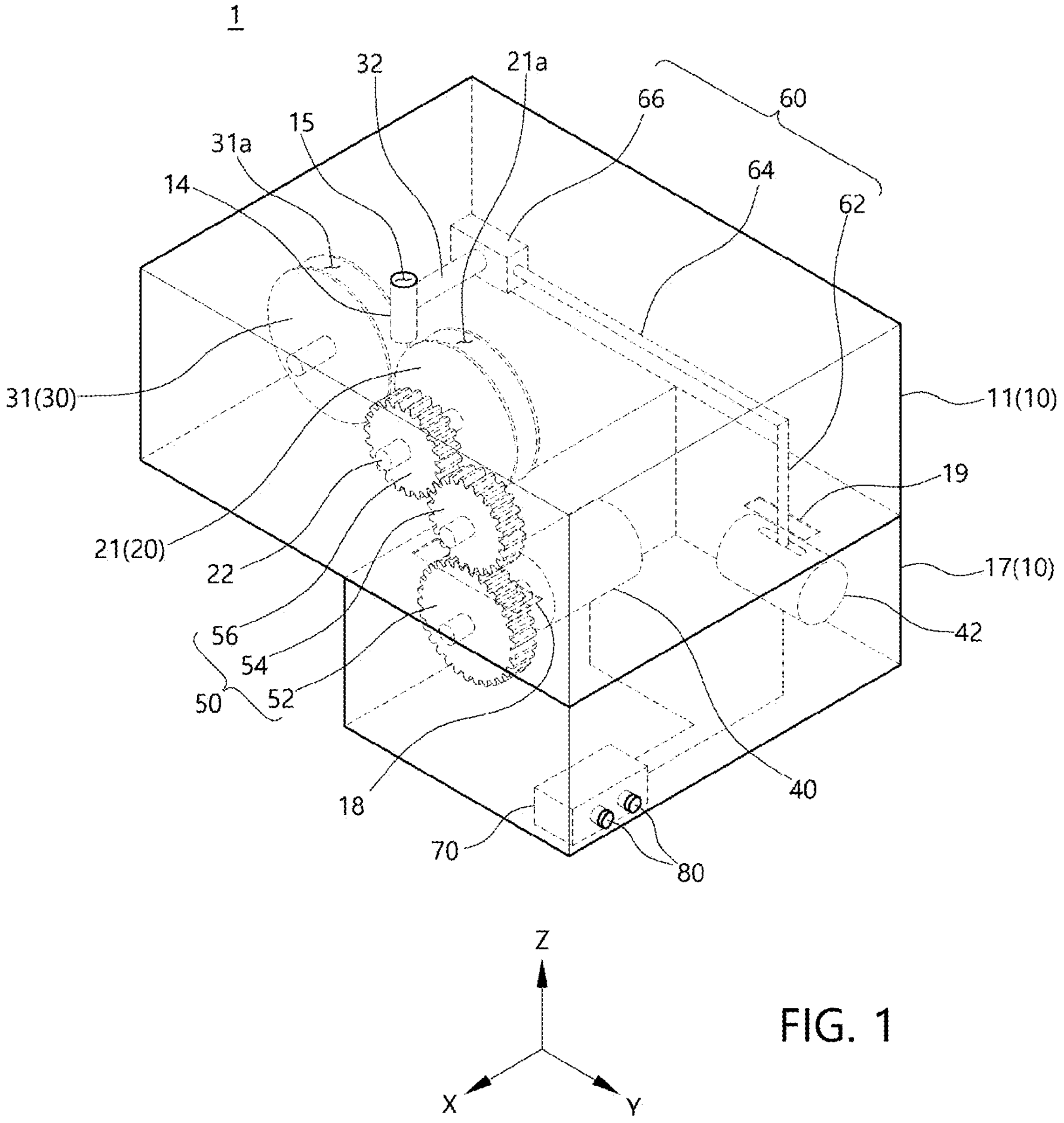
FIG. 1 is a perspective view of a tubular member moving apparatus according to a first embodiment of the present disclosure.

Hereinafter, an embodiment of the present disclosure will be described in detail with reference to the accompanying drawings so that those skilled in the technical field to which the present disclosure pertains may easily carry out the embodiment. The present disclosure may be implemented in various different ways, and is not limited to the embodiments described herein. In the drawings, a part irrelevant to the description will be omitted to clearly describe the present disclosure, and the same or similar constituent elements will be designated by the same reference numerals throughout the specification.

Terms or words used in the specification and the claims should not be interpreted as being limited to a general or dictionary meaning and should be interpreted as a meaning and a concept which conform to the technical spirit of the present disclosure based on a principle that an inventor can appropriately define a concept of a term in order to describe his/her own invention.

In the present application, it will be appreciated that terms "including" and "having" are intended to designate the existence of characteristics, numbers, steps, operations, constituent elements, and components described in the specification or a combination thereof, and do not exclude a possibility of the existence or addition of one or more other characteristics, numbers, steps, operations, constituent elements, and components, or a combination thereof in advance.

Unless otherwise specified, a case in which one constituent element is disposed at "a front side," "a rear side," "an upper side," or "a lower side" of another constituent element includes not only a case in which one constituent element is disposed at "the front side," "the rear side," "the upper side," or "the lower side" of another constituent element while directly adjoining another constituent element, but also a case in which a further constituent element is disposed between one constituent element and another constituent element. In addition, unless otherwise specified, a case in which one constituent element is "connected to" another constituent element includes not only a case in which one constituent element and another constituent element are directly connected to each other, but also a case in which one constituent element and another constituent element are indirectly connected to each other.

A tubular member moving apparatus according to an embodiment of the present disclosure is a tubular member moving apparatus, in which a driven roller unit including a driven roller may bring a tubular member into close contact with the driving roller, thereby moving the tubular member by using a frictional force generated between the tubular member and the driving roller.

In this case, the tubular member moving apparatus according to the embodiment of the present disclosure may include a roller operating unit capable of moving the driven roller toward or away from the driving roller, and the roller operating unit may bring the tubular member into close contact with the driving roller or separate the tubular member from the driving roller. Therefore, an automatic mode may be easily switched to a manual mode or vice versa, and a contact area between the tubular member and the driving roller may increase.

Meanwhile, for example, the tubular member may be a member elongated and having a diameter of several millimeters (mm) to several centimeters (cm). A diameter of the tubular member, which may be moved by the tubular member moving apparatus, may be variously selected depending on sizes of components of the tubular member moving apparatus.

In one embodiment, the tubular member may be a part of an endoscope or a part of a surgical tool or device used together with the endoscope. However, the tubular member moving apparatus for moving a tubular member according to the embodiment of the present disclosure is not limited to the configuration for moving a part of an endoscopic device or a part of a device for an endoscope.

Hereinafter, a tubular member moving apparatus according to a first embodiment of the present disclosure will be described.

Figure 2:
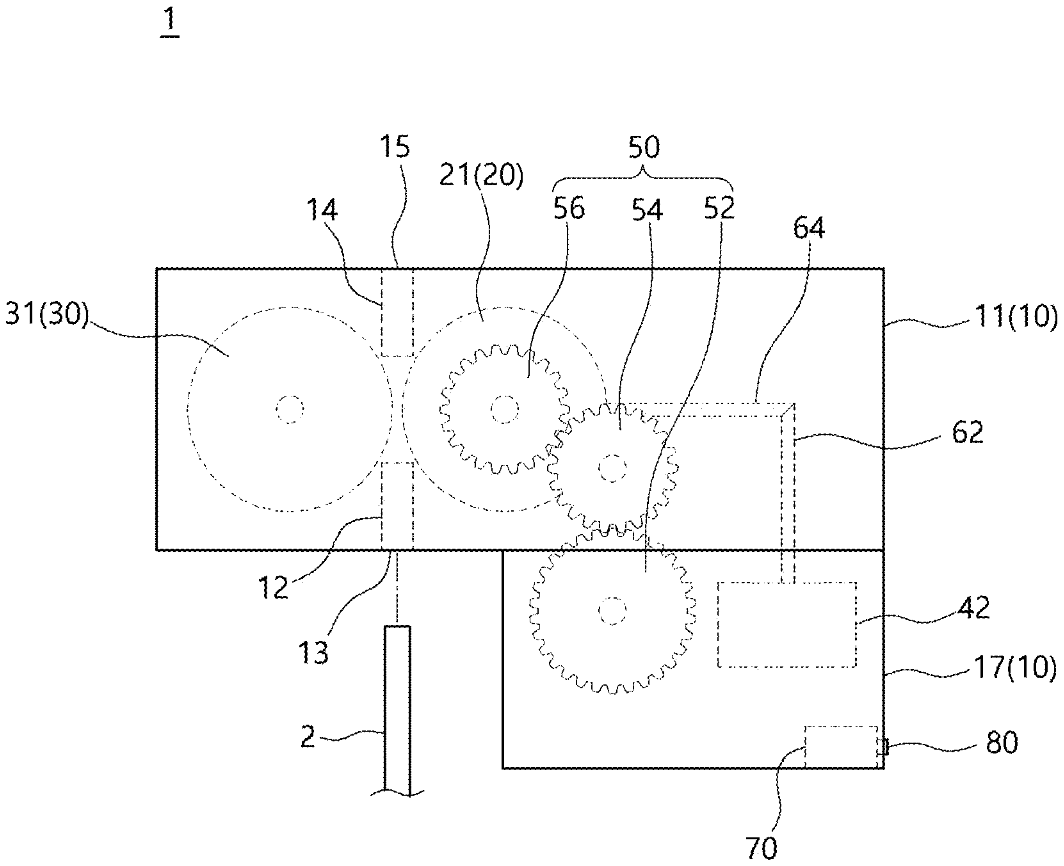
FIG. 2 is a front view of the tubular member moving apparatus according to the first embodiment of the present disclosure.
Figure 3:
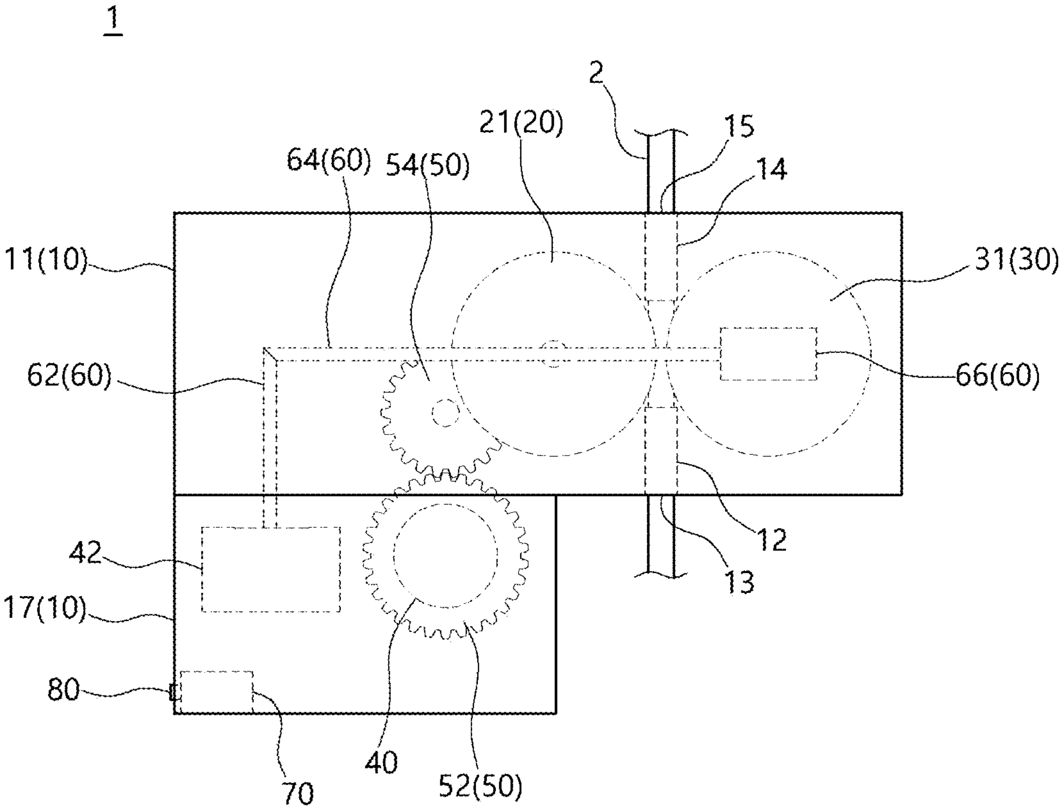
FIG. 3 is a rear view of the tubular member moving apparatus according to the first embodiment of the present disclosure.
Figure 4:
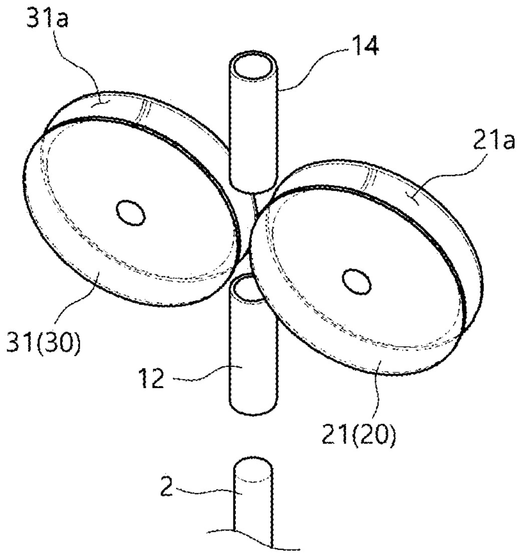
FIG. 4 is a view illustrating a roller, a tubular member, and a guide member of the tubular member moving apparatus according to the first embodiment of the present disclosure, in which (a) is a perspective view, and (b) is a top plan view.
Figure 4:
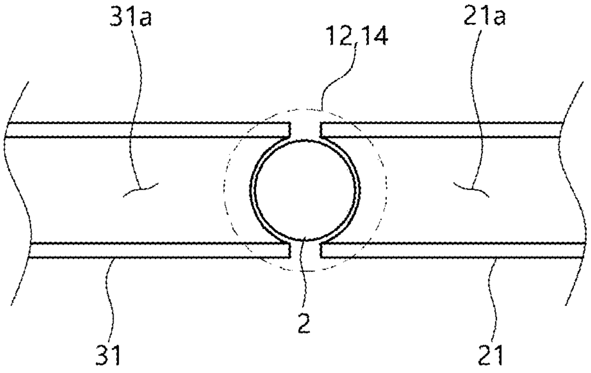

FIG. 1 is a perspective view of a tubular member moving apparatus according to a first embodiment of the present disclosure. FIG. 2 is a front view of the tubular member moving apparatus according to the first embodiment of the present disclosure. FIG. 3 is a rear view of the tubular member moving apparatus according to the first embodiment of the present disclosure. FIG. 4 is a view illustrating a roller, a tubular member, and a guide member of the tubular member moving apparatus according to the first embodiment of the present disclosure, in which (a) is a perspective view, and (b) is a top plan view.

In this case, in FIGS. 1 to 3, the components projected through first and second housings are indicated by dotted lines.

Referring to FIGS. 1 and 2, a tubular member moving apparatus 1 according to a first embodiment of the present disclosure may include a housing 10, a driving roller unit 20, a driven roller unit 30, a first actuator 40, a second actuator 42, a power transmitting member 50, and a roller operating unit 60.

The housing 10 includes a first housing 11 and a second housing 17. The first housing 11 accommodates and protects the driving roller unit 20, the driven roller unit 30, and guide members 12 and 14. In this case, the driving roller unit 20 includes a driving roller 21. The driven roller unit 30 includes a driven roller 31.

The first housing 11 has a box-shaped structure having a sufficient size so that the driving roller 21, the driven roller 31, and the guide members 12 and 14 may be installed in the first housing 11.

Referring to FIGS. 1 and 2, the driving roller 21 is positioned at a central portion of the first housing 11, and the driven roller 31 and the driving roller 21 are positioned at an appropriate distance so that the guide members 12 and 14 may be positioned between the two rollers 21 and 31. The appropriate distance will be described below.

Referring to FIG. 4, the driving roller 21 and the driven roller 31 are each provided in the form of a circular plate-shaped member having a predetermined thickness. Grooves **21*a* and 31*a* corresponding to an outer peripheral portion of the tubular member 2 are respectively formed in an outer peripheral surface of the driving roller 21 and an outer peripheral surface of the driven roller 31**.

In the present embodiment, the grooves **21*a* and 31*a* of the driving and driven rollers 21 and 31 each have a semi-circular shape corresponding to a shape of the tubular member 2. Further, the grooves 21*a* and 31*a* of the driving and driven rollers 21 and 31 each have an elliptical shape or the like corresponding to a cross-sectional shape of the tubular member 2**.

Referring to (b) of FIG. 4, when the roller grooves **21*a* and 31*a* are formed to correspond to the outer peripheral portion of the tubular member 2, the most parts of the outer peripheral portion of the tubular member 2 adjoin the outer peripheral surfaces of the rollers 21 and 31, such that the contact area between the tubular member 2 and the outer peripheral surfaces of the rollers 21 and 31** may increase.

In addition, friction members configured as rubber pads or the like may be installed on the outer peripheral surfaces of the rollers 21 and 31, such that frictional coefficients between the tubular member 2 and the outer peripheral surfaces of the rollers 21 and 31 may increase.

Referring to FIG. 1, roller shafts 22 and 32 are rotatably installed at centers of the rollers 21 and 31, respectively.

The roller shafts 22 and 32 may each be a member having a rod shape, extending to a predetermined length, and made of metal or plastic having a predetermined strength. The driving roller shaft 22 is installed at a center of the first housing 11 and fixed in an x-axis direction. The driven roller shaft 32 and the driving roller shaft 22 are installed in parallel with each other at a predetermined distance in a y-axis direction.

Two opposite ends of each of the roller shafts 22 and 32 are rotatably installed on an inner wall of the first housing 11. To this end, bearing members may be provided between the first housings 11 and the roller shafts 22 and 32.

Referring to FIG. 1, a gear is installed on the driving roller shaft 22, disposed at a predetermined distance from the driving roller 21 in the x-axis direction, and rotates the driving roller 21 by receiving a rotational force.

A third connection member 66 is installed on the driven roller shaft 32 and disposed at a predetermined distance from the driven roller 31 in a direction opposite to the x-axis direction. The third connection member 66 transmits a force that may move the driven roller shaft 32 in the y-axis direction. In this case, a bearing member is provided between the third connection member 66 and the driven roller shaft 32, such that the third coupling member 66 and the driven roller shaft 32 may rotate relative to each other. The third connection member 66 will be described below.

Referring to FIG. 4, the guide members 12 and 14 may include the first guide member 12 and the second guide member 14.

In the present embodiment, the guide members 12 and 14 are positioned between the driving roller 21 and the driven roller 31. The first guide member 12 and the second guide member 14 may be spaced apart from each other so that the tubular member 2 may come into direct contact with the outer peripheral surfaces of the driving and driven rollers 21 and 31.

As another embodiment, the first guide member 12 and the second guide member 14 may be integrated, and through-holes may be formed in only portions of the outer peripheral surfaces of the guide members 12 and 14 that come into contact with the tubular member 2 and the rollers 21 and 31.

Referring to FIGS. 3 and 4, an inlet 13 and an outlet 15 through which the tubular member 2 penetrates the housing are formed in upper and lower surfaces of the first housing 11. The guide members 12 and 14 connect the outlet 15 and the inlet 13 of the first housing 11 so that the tubular member 2 may penetrate the first housing 11.

According to the present embodiment, the guide members 12 and 14 are formed in a straight shape and connect the inlet 13 and the outlet 15. However, in another embodiment, the guide members 12 and 14 may be formed in a curved shape depending on the flexibility of the tubular member 2, the positions of the inlet 13 and the outlet 15, and the arrangement of the internal components of the first housing 11.

In addition, in still another embodiment, the guide members 12 and 14 may protrude to the outside of the first housing 11 so that the tubular member 2 may be guided to the inside of the first housing 11 by the guide members 12 and 14.

Meanwhile, the second housing 17 has a box-shaped structure having a sufficiently large size so as to accommodate and protect the first actuator 40 and the second actuator 42 therein.

Referring to FIG. 1, the second housing 17 may be installed at a right lower side of the first housing 11. However, a relative position between the first housing 11 and the second housing 17 may be appropriately set in accordance with the convenience for the user who uses an endoscopic device or in accordance with the arrangement of the components of the tubular member moving apparatus 1.

For example, as illustrated in FIG. 2, the second housing 17 may be installed at a right lower side or a left lower side of the inlet 13 of the first housing 11 in consideration of a surgical or medical environment of a practitioner who uses an endoscope for a human body.

As illustrated in FIG. 1, the first actuator 40 is disposed at a left side of the inside of the second housing 17, and the second actuator 42 is disposed at a rear side of the first actuator 40.

The first actuator 40 generates driving power for rotating the driving roller 21. The second actuator 42 generates driving power for linearly moving the driven roller 31 in the y-axis direction. In the present embodiment, the first actuator 40 is a rotary motor. The second actuator 42 is a linear motor capable of linearly moving a particular member.

The power transmitting member 50 is positioned between the first actuator 40 and the driving roller 21 and transmits driving power. The roller operating unit 60 is positioned between the second actuator 42 and the driven roller 21 and transmits driving power.

In this case, a rotary shaft is provided at one side of the first actuator 40 and rotated by the first actuator 40, and the rotary shaft is disposed in parallel with The roller shafts 22 and 32 in the x-axis direction.

Referring to FIGS. 1 and 2, in the present embodiment, the first actuator 40 transmits driving power to the driving roller shaft 22 through the power transmitting member 50 installed in the first housing 11.

In this case, the power transmitting member 50 includes first to third gears 52, 54, and 56. The first to third gears 52, 54, and 56 may each be configured as a spur gear. The first gear 52 is provided on the rotary shaft of the first actuator 40, and the third gear 56 is provided on the driving roller shaft 22. The second gear 54 is connected to the first and third gears 52 and 56.

A ratio between a rotational speed of the first actuator 40 and a rotational speed of the driving roller 21, a rotation direction, and a torque ratio may be adjusted depending on the number of teeth of the first to third gears 52, 54, and 56.

However, the first to third gears 52, 54, and 56 of the power transmitting member 50 are not limited to the spur gear. For example, the first and third gears 52 and 56 may each be configured as a worm wheel, and the second gear 54 may be configured as a worm shaft. In this case, backlash may decrease, and a movement amount of the tubular member 2 may be accurately controlled.

In this case, referring to FIG. 1, rectangular openings 18 are formed in surfaces of the first and second housings 11 and 17 that face each other. The interior of the first housing 11 and the interior of the second housing 17 communicate with each other through the openings 18. One side of the first gear 52 installed on the first actuator 40 is connected to the second gear 54 through the openings 18.

Meanwhile, referring to FIG. 3, the roller operating unit 60 is provided. The roller operating unit 60 serves to transmit driving power, which is generated by the second actuator 42, to the driven roller 31. The roller operating unit 60 includes first, second, and third connection members 62, 64, and 66. In this case, the roller operating unit 60 may be made of a material such as metal having predetermined rigidity.

The first connection member 62 extends in a z-axis direction from one side of the second actuator 42 to the inside of the first housing 11. The second connection member 64 extends in the x-axis direction in the second housing 11. In this case, one end of the first connection member 62 and one end of the second connection member 64 are coupled to each other.

As described above, the third connection member 66 is coupled to the driven roller shaft 32 so as to be rotatable relative to the driven roller shaft 32. The other end of the second connection member 64 is coupled to the third connection member 66.

However, the coupling structures between the first to third connection members 62, 64, and 66 are not particularly limited as long as the driving power of the second actuator 42 may be transmitted to the driven roller 31. For example, a sliding coupling method using a guide groove and a guide protrusion may be applied. In addition, the roller operating unit 60 may be integrally formed.

Referring to FIGS. 1 and 3, when the second actuator 42 linearly moves the roller operating unit 60, the driven roller central shaft 32 coupled to the third connection member 66 of the roller operating unit 60 is linearly moved, and therefore, the driven roller 31 is linearly moved.

In embodiments, a separate guide unit may be provided on the inner wall of the first housing 11 and guide the movement of the driven roller 31 in the y-axis direction.

In this case, guide holes 19 are formed in the surfaces of the first and second housings 11 and 17 that face each other. The guide holes 19 allow the first connection member 62 penetrating the sidewalls of the first and second housings 11 and 17 to smoothly move.

Meanwhile, in the present embodiment, a distance between the first actuator 40 and the driving roller 21 may be shorter than a distance between the second actuator 42 and the driven roller 31. Therefore, it is possible to simplify the sizes and internal design of the components and improve power transmission efficiency of the power transmitting member 50. In addition, the internal components may be compactly disposed, which may provide the tubular member moving apparatus 1 that has a small width in a forward/rearward direction and is light in weight.

In this case, the distance between the first actuator 40 and the driving roller 21 may be as short as possible in order to effectively transmit driving power to the driving roller 21. In contrast, because the roller operating unit 60 just needs to perform the operation of linearly moving the driven roller 31, the disadvantages such as deterioration in power transmission efficiency and the simplification of design are small even though the distance between the second actuator 42 and the driven roller 31 comparatively increases.

Therefore, in the present embodiment, the distance between the first actuator 40 and the driving roller 21 may be shorter than the distance between the second actuator 42 and the driven roller 31.

However, the arrangement of the rollers 21 and 31 and the actuators 40 and 42 are provided and may be appropriately changed to conform to a working environment in which the tubular member moving apparatus 1 is used, properties of components constituting the power transmitting member 50 and the roller operating unit 60, and manufacturing processes.

Hereinafter, the automatic mode and the manual mode of the tubular member moving apparatus according to the first embodiment of the present disclosure will be described.

Figure 5:
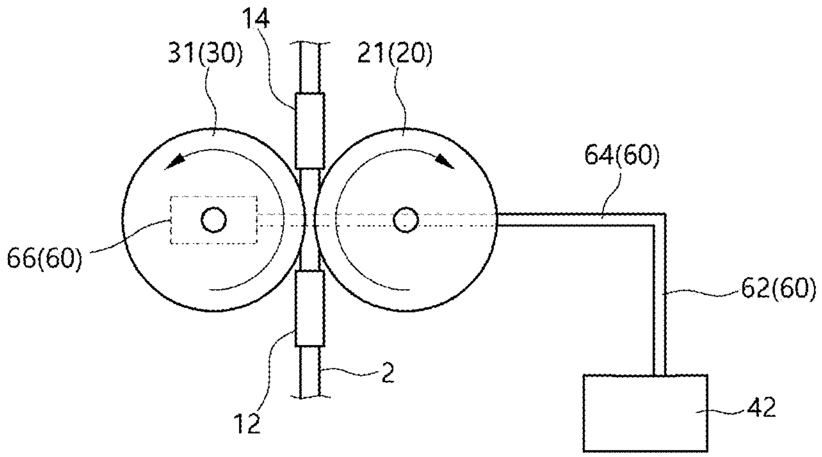
FIG. 5 is a view illustrating a second actuator and a roller according to a manual mode and an automatic mode of the tubular member moving apparatus according to the first embodiment of the present disclosure, in which (a) is a view illustrating a state of the automatic mode, and (b) is a view illustrating a state of the manual mode.
Figure 5:
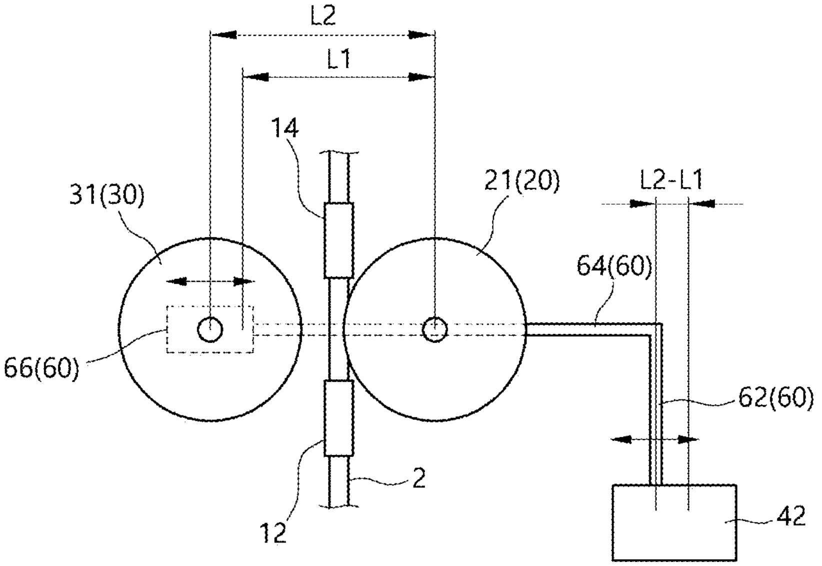

FIG. 5 is a view illustrating the second actuator and the roller according to the manual mode and the automatic mode of the tubular member moving apparatus according to the first embodiment of the present disclosure, in which (a) is a view illustrating a state of the automatic mode, and (b) is a view illustrating a state of the manual mode.

In the present embodiment, the position of the driving roller 21 is fixed, and the driving roller 21 does not move in the first housing 11. However, the driven roller 31 may be moved in the horizontal direction by the second actuator 42.

In this case, a distance between the driving roller central shaft 22 and the driven roller central shaft 32 is L1 in the automatic mode, and a distance between the driving roller central shaft 22 and the driven roller central shaft 32 is L2 in the manual mode. Therefore, the second actuator 42 may move the driven roller 31 by a distance of ‘L2−L1’.

Referring to (a) of FIG. 5, since a distance between the driving roller 21 and the driven roller 31 is short in the automatic mode, the outer peripheral surface of the driven roller 31 may support the tubular member 2 that receives a force while adjoining the outer peripheral surface of the driving roller 21.

Therefore, the outer peripheral surface of the driving roller 21 may generate a vertical drag force in the horizontal direction against the tubular member 2. Therefore, the tubular member 2 is moved along the outer peripheral surface of the driving roller 21 in the upward direction based on FIG. 5 by the frictional force between the driving roller 21 and the tubular member 2. Hereinafter, the position of the driven roller 31 in the automatic mode is referred to as a ‘first position’.

When the driving roller 21 rotates clockwise, the tubular member 2 is inserted and moved in the direction toward the outlet. When the driving roller 21 rotates counterclockwise, the tubular member 2 is extracted in the direction toward the inlet. Therefore, according to the present disclosure, the tubular member 2 may be automatically moved.

In this case, the distance between the driving roller 21 and the driven roller 31 may of course be appropriately adjusted so that the tubular member 2 may be moved by the frictional force. When the distance between the rollers 21 and 31 is too short, the tubular member 2 is trapped between the rollers 21 and 31, and the tubular member 2 cannot be moved. When the distance between the rollers 21 and 31 is long, the vertical drag force is not generated, and the movement of the tubular member 2 by the frictional force is not implemented.

Meanwhile, referring to (b) of FIG. 5, in the manual mode, the driven roller 31 may be moved by ‘L2−L1’ in the direction away from the driving roller 21. Therefore, because a space is formed between the tubular member 2 and the driven roller 31, a vertical drag force cannot be generated. Therefore, the outer peripheral surfaces of the rollers 21 and 31 cannot press the tubular member 2.

Therefore, because the frictional force cannot be generated between the rollers 21 and 31 and the tubular member 2, the movement of the tubular member 2 by the driving power of the first actuator 40 cannot be implemented. Hereinafter, the position of the driven roller 31 in the manual mode is referred to as a ‘second position’. In this case, the user may adjust the movement of the tubular member 2 with his/her hand.

As described above, according to the tubular member moving apparatus 1 according to the present embodiment, the user may automatically move the tubular member 2 by a targeted length in the automatic mode, thereby mitigating physical burden. In addition, thereafter, the user may switch the mode of the tubular member moving apparatus 1 to the manual mode and precisely and directly move the tubular member 2, thereby precisely adjusting the movement amount of the tubular member 2.

Meanwhile, referring back to FIG. 1, the tubular member moving apparatus 1 according to the first embodiment of the present disclosure may include a control unit 70. The control unit 70 may adjust and switch the mode to the automatic mode and the manual mode by moving the driven roller 31 to the first position or the second position by controlling the second actuator 42. The control unit 70 may automatically move the tubular member 2 by rotating the driving roller 21 by controlling the first actuator 40.

The control unit 70 may be installed between the first actuator 40 and the second actuator 42 in the second housing 17. The control unit 70 may be electrically connected to the actuators 40 and 42 through an electric communication wire or in a wireless communication manner. Alternatively, the control unit 70 may be separately provided outside the first housing 11 or the second housing 17.

Referring to FIG. 1, a manipulation unit 80 is provided at one side of the control unit 70. In this case, the manipulation unit 80 may include a mode switching button.

Referring to FIG. 4, when the user pushes the mode switching button in the state in which the driven roller 31 is positioned at the first position in the automatic mode, the first actuator 40 may operate and move the driven roller 31 to the second position, thereby switching the mode of the tubular member moving apparatus 1 to the manual mode.

On the contrary, when the user pushes the mode switching button in the state in which the driven roller 31 is positioned at the second position in the manual mode, the first actuator 40 may operate and move the driven roller 31 to the first position, thereby switching the mode of the tubular member moving apparatus 1 to the automatic mode.

In addition, the manipulation unit 80 may include up and down buttons. When the user selects the up button between the up and down buttons, the first actuator 40 may operate and rotate the driving roller 21 clockwise, thereby moving the tubular member 2 from the inlet 13 to the outlet 15.

On the contrary, when the user selects the down button, the first actuator 40 may operate and rotate the driving roller 21 counterclockwise, thereby moving the tubular member 2 from the outlet 15 to the inlet 13.

In addition, when the up and down buttons are selected by the user's manipulation, the control unit 70 may move the driven roller 31 to the first position by controlling the second actuator 42, rotate the driving roller 21 by a preset number of times by controlling the first actuator 40, and then move the driven roller 31 to the second position by controlling the second actuator 42. Therefore, the tubular member moving apparatus 1 according to the present embodiment may accurately move the tubular member 2 by a preset movement amount.

In the present embodiment, the manipulation unit 80 may be configured as a button member protruding to the outside of the control unit 70. The manipulation unit 80 may include a display screen installed on an outer surface of the control unit 70, and the user's selection may be implemented by touching the display screen.

Figure 6:
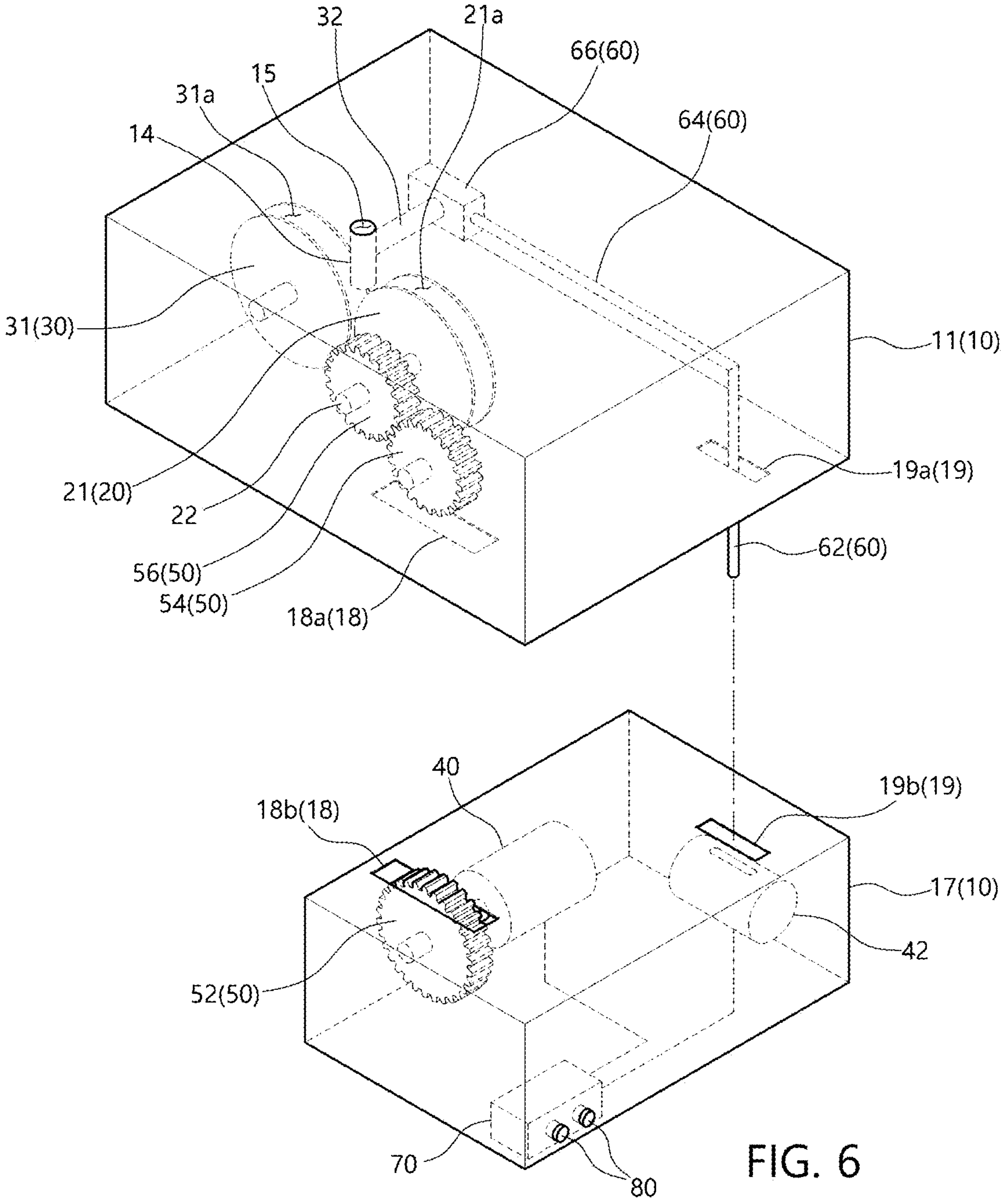
FIG. 6 is a view illustrating a state in which a first housing and a second housing of the tubular member moving apparatus according to the first embodiment of the present disclosure are separated.
Figure 7:
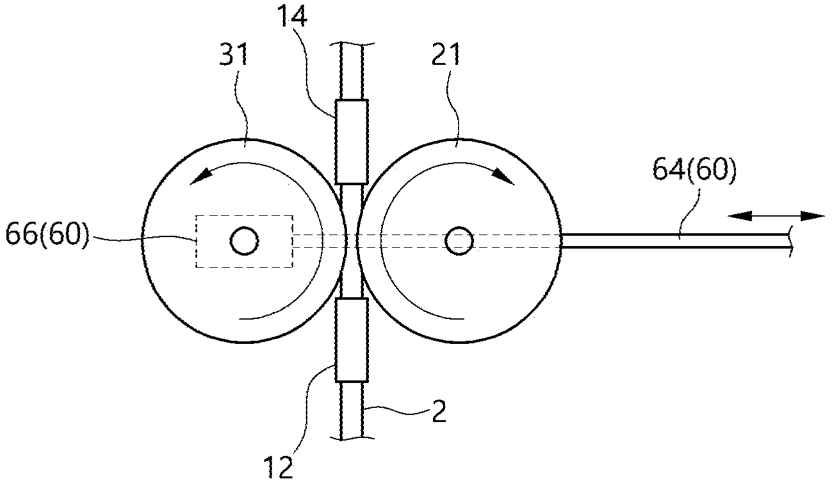
FIG. 7 is a view illustrating a state in which a connection member of the tubular member moving apparatus according to the first embodiment of the present disclosure is manually moved.

FIG. 6 is a view illustrating a state in which the first housing and the second housing of the tubular member moving apparatus according to the first embodiment of the present disclosure are separated. FIG. 7 is a view illustrating a state in which the connection member of the tubular member moving apparatus according to the first embodiment of the present disclosure is manually moved. In this case, the components projected through the first and second housings are indicated by dotted lines.

Referring to FIG. 6, in the present embodiment, the first housing 11 and the second housing 17 may be separably coupled. In this case, various fastening methods such as a coupling method using a bolt and a nut and a coupling method using a sliding structure may be used as the method of separably coupling the housings.

In this case, when the first housing 11 and the second housing 17 are separated, the first gear 52 positioned in the first housing 11 and the second gear 54 positioned in the second housing 17 may be separated.

In addition, when the first housing 11 and the second housing 17 are separated, the first connection member 62 and the second actuator 42 may be separated. However, when the first housing 11 and the second housing 17 are separated, the first connection member 62 and the second connection member 64 may be separated.

Referring to FIG. 7, when the second connection member 64 is separated from the second actuator 42, the user may move the third connection member 66 and the driven roller 31 by manually moving the second connection member 64.

One end of the second connection member 64 may protrude to the outside of the first housing 11 or an additional component for the user's manipulation may be coupled so that the user may manually move the second connection member 64 as described above.

When the user may manually move the second connection member 64 as described above, the user may manually switch the mode of the tubular member moving apparatus 1 to the manual mode or the automatic mode without the second actuator 42.

Figure 8:
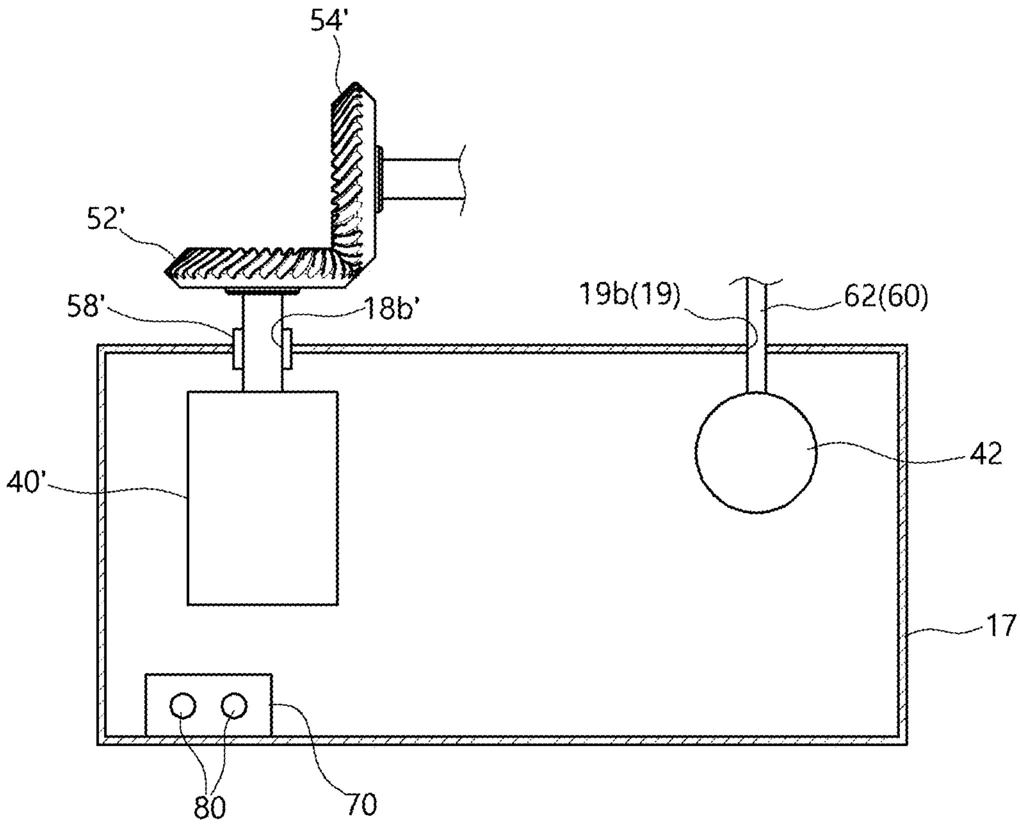
FIG. 8 is a view for explaining a modified example of the tubular member moving apparatus according to the first embodiment of the present disclosure.

FIG. 8 is a view for explaining a modified example of the tubular member moving apparatus according to the first embodiment of the present disclosure. In this case, a cross-section of the second housing is illustrated so that the interior of the second housing is visible.

Referring to FIG. 8, in the modified example of the first embodiment of the present disclosure, a first actuator 40' installed in the second housing 17 has a rotary shaft configured to penetrate an opening **18*b*' of the second housing 17, and a sealing member 58'** is installed between the rotary shaft and the opening.

First and second gears 52' and 54' may be coupled to the rotary shaft of the first actuator 40' and transmit power. In addition, a sealing member may also be installed between the guide groove **19*b* and the first connection member 62 coupled to the second actuator 42**.

In embodiments, the sealing member may be made of a publicly-known material such as rubber. Therefore, the second housing 17 in which the first actuator 40 and the second actuator 42 are installed may be isolated from the outside, thereby preventing contamination.

Referring back to FIG. 6, according to the tubular member moving apparatus 1 according to the first embodiment of the present disclosure, the first housing 11 configured to accommodate the driving roller 21 and the driven roller 31 for moving the tubular member 2 and the second housing 17 configured to accommodate the first actuator 40 and the second actuator 42 are separably coupled. That is, the operating part and the driving part may be separably provided.

Therefore, according to the present embodiment, the first housing 11 may be separated and then cleaned, thereby preventing damage to the actuators 40 and 42 and the control unit 70 that may be caused during the cleaning process.

For example, in the case in which the tubular member 2 is a part of the endoscope for a human body, the tubular member 2 contaminated by tumor, blood, or the like may contaminate the rollers 21 and 31 and the like. Therefore, the rollers 21 and 31 need to be cleaned so that the tubular member moving apparatus 1 may be used for surgical or medical procedures for other patients.

In this case, according to the tubular member moving apparatus 1 according to the present embodiment, the user may separate and clean the first housing 11, thereby preventing damage to the actuators 40 and 42 and the control unit 70 that may be caused during the cleaning process.

In addition, according to the tubular member moving apparatus 1 according to the first embodiment of the present disclosure, the user may easily separate and couple the first housing 11 and the second housing 17 in a situation in which the first housing 11 and the second housing 17 need to be separated such as a situation in which the first housing 11 and the second housing 17 need to be repaired, replaced, or inspected.

Hereinafter, a tubular member moving apparatus according to a second embodiment of the present disclosure will be described.

Figure 9:
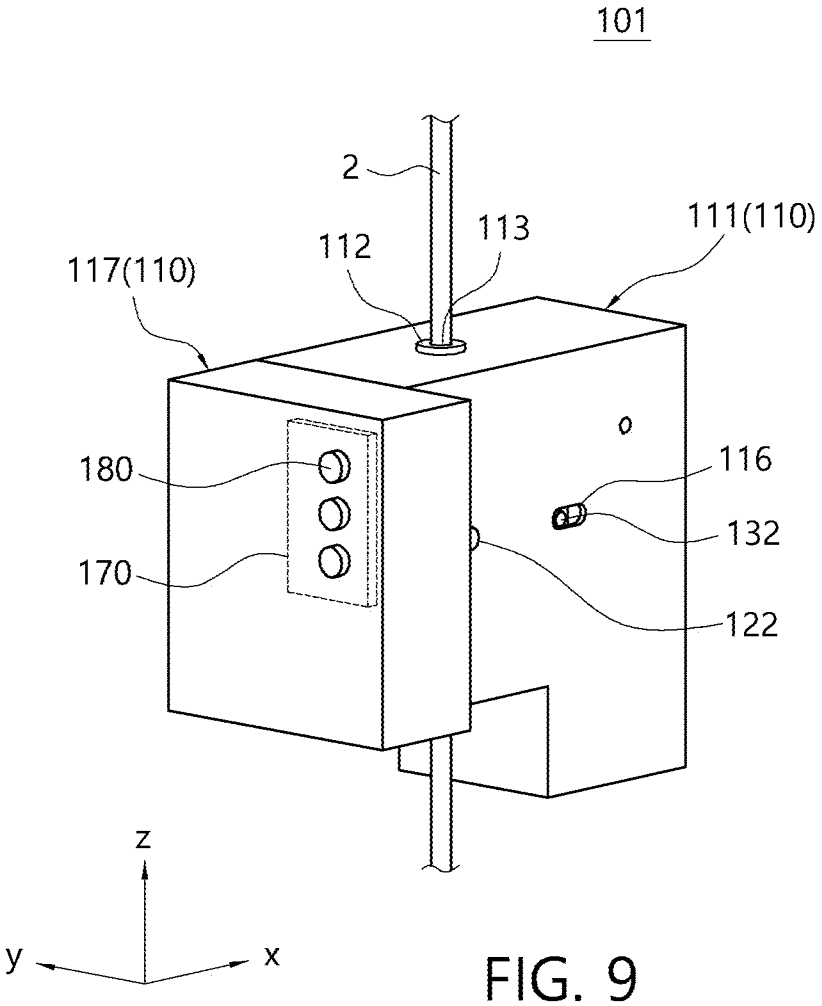
FIG. 9 is a perspective view of a tubular member moving apparatus according to a second embodiment of the present disclosure.
Figure 10:
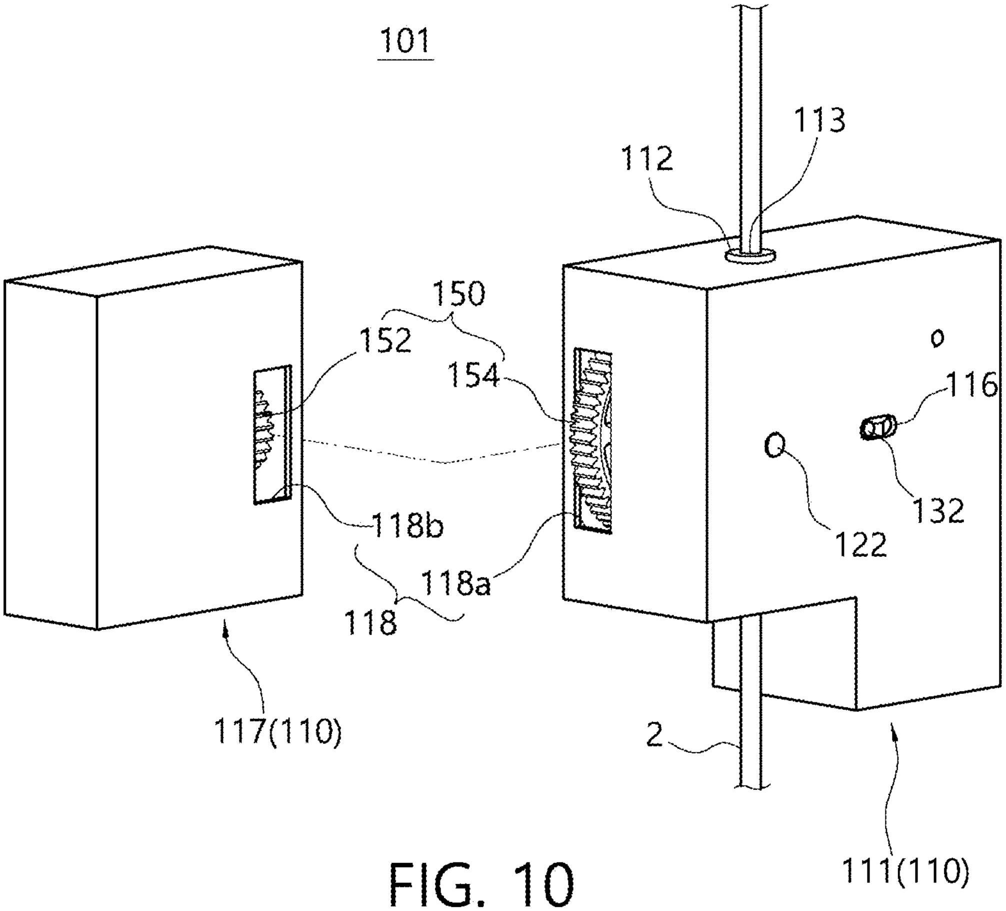
FIG. 10 is an exploded perspective view of the tubular member moving apparatus according to the second embodiment of the present disclosure.
Figure 11:
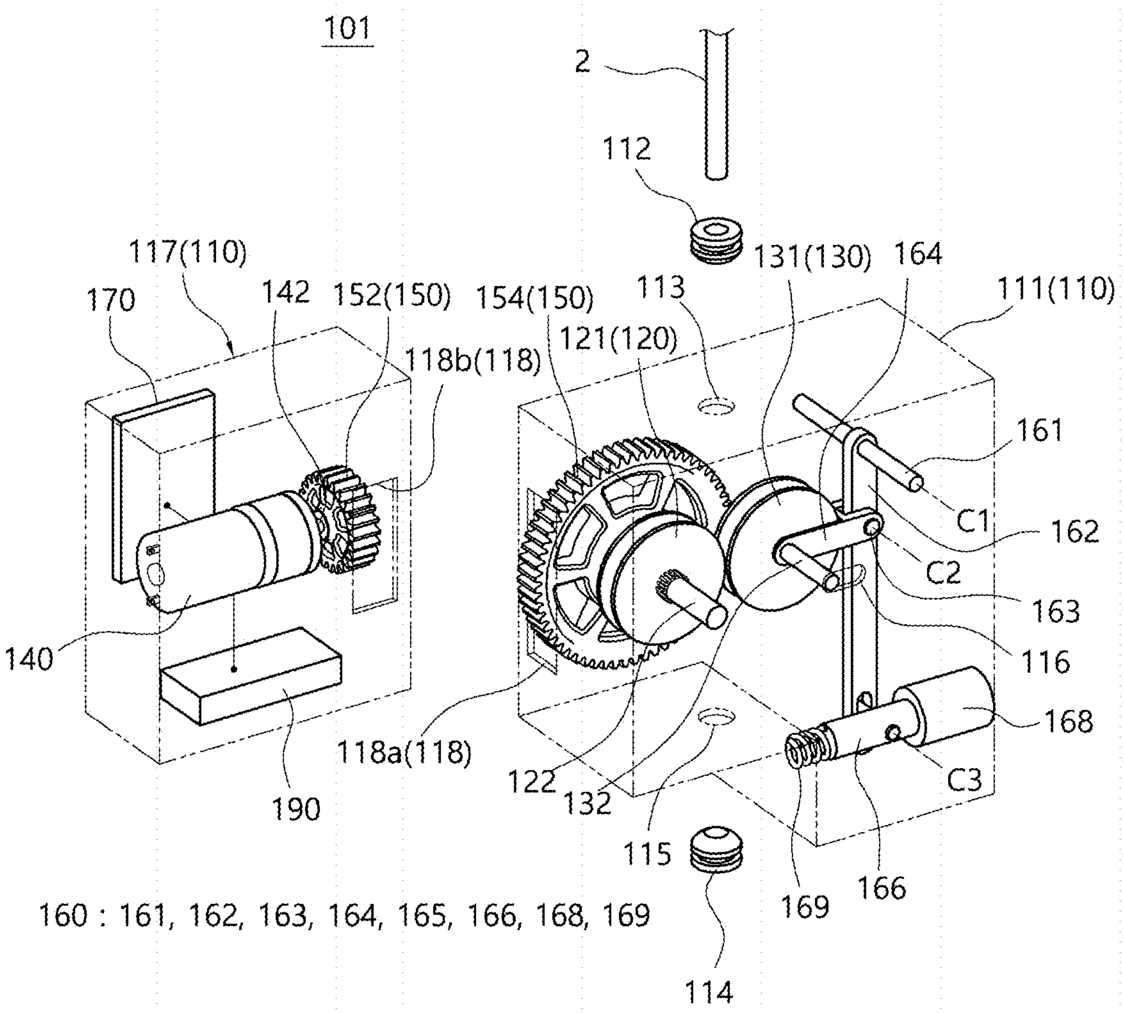
FIG. 11 is an exploded perspective view of the tubular member moving apparatus according to the second embodiment of the present disclosure.
Figure 12:
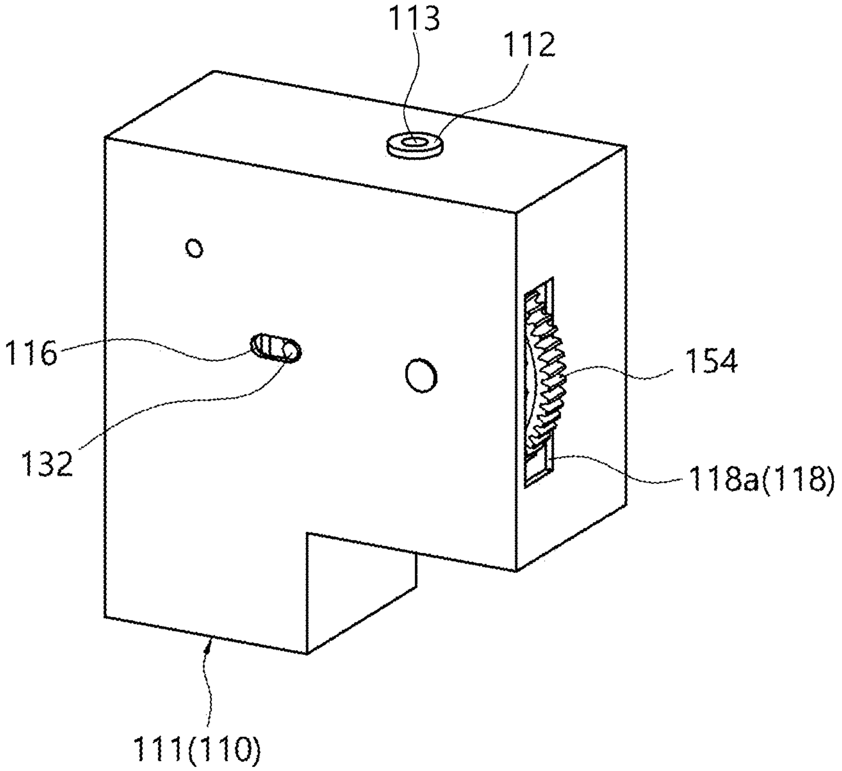
FIG. 12 is a perspective view of a first housing and components accommodated in the first housing of the tubular member moving apparatus according to the second embodiment of the present disclosure when viewed at another angle.

FIG. 9 is a perspective view of a tubular member moving apparatus according to a second embodiment of the present disclosure. FIG. 10 is an exploded perspective view of the tubular member moving apparatus according to the second embodiment of the present disclosure. FIG. 11 is an exploded perspective view of the tubular member moving apparatus according to the second embodiment of the present disclosure. FIG. 12 is a perspective view of a first housing and components accommodated in the first housing of the tubular member moving apparatus according to the second embodiment of the present disclosure when viewed at another angle.

In this case, in FIG. 11, the first and second housing are indicated by dotted lines, and the components projected through the first and second housing are indicated by solid lines.

In the following description with reference to the drawings, the directions are defined and described on the basis of coordinate axes illustrated in FIG. 9. More specifically, a positive z-axis direction is defined as an upward direction, and a negative z-axis direction is defined as a downward direction. A positive y-axis direction is defined and described as a rearward direction, and a negative y-axis direction is defined and described as a forward direction. A positive x-axis direction is defined as a rightward direction, and a negative x-axis direction is defined as a leftward direction.

Referring to FIGS. 9 to 12, the moving apparatus according to the second embodiment of the present disclosure may include a housing 110, a driving roller unit 120, a driven roller unit 130, an actuator 140, a power transmitting member 150, a roller operating unit 160, a control unit 170, a manipulation unit 180, and an energy storage means 190.

Hereinafter, driving parts mean components configured to provide and transmit driving power for moving the tubular member 2 and components related to the above-mentioned components, and operating parts mean components configured to move the tubular member 2 by receiving driving power from the driving part and components related to the above-mentioned components.

That is, the driving parts include the actuator 140, the control unit 170, the manipulation unit 180, and the energy storage means 190, and the operating parts include the driving roller unit 120, the driven roller unit 130, and the roller operating unit 160.

The housing 110 includes a first housing 111 and a second housing 117 separably coupled to each other. The first housing 111 accommodates the operating parts therein, and the second housing 117 accommodates the driving parts therein.

Meanwhile, the driving roller unit 120 includes a driving roller 121. The driven roller unit 130 includes a driven roller 131.

Referring to FIGS. 9 and 10, the second housing 117 is disposed at the left side of the first housing 111. The first housing 111 includes a horizontal portion having a rectangular parallelepiped shape and extending in a horizontal direction, and a vertical portion having a rectangular parallelepiped shape and extending downward from a right portion of the horizontal portion.

The tubular member 2 may penetrate a left portion of the horizontal portion of the first housing 111. In this case, the tubular member 2 may be arranged in the upward/downward direction and spaced apart from the vertical portion of the first housing 111 at a predetermined distance.

Referring to FIG. 11, an internal space of the horizontal portion of the first housing 111 and an internal space of the vertical portion of the first housing 111 communicate with each other. The horizontal portion accommodates the driving roller 121 and the driven roller 131, and the right portion of the horizontal portion and the vertical portion accommodate the roller operating unit 160.

In this case, the driving roller 121 rotates in place, and the driven roller 131 and the roller operating unit 160 linearly move in the leftward/rightward direction. That is, the components accommodated in the first housing 111 do not move in the forward/rearward direction.

Therefore, a thickness of the first housing 111 in the forward/rearward direction may be smaller than a width of the first housing 111 in the leftward/rightward direction. Therefore, in the present embodiment, the first housing 111 may be compactly manufactured to be small in size, thereby improving spatial utilization and reducing weight and manufacturing costs.

In addition, a width of the horizontal portion of the first housing 111 is sufficient to accommodate the driving roller 121 and the driven roller 131, and a length of the vertical portion is sufficient to accommodate a lower portion of the roller operating unit 160.

Referring to FIG. 11, an outlet 115 and an inlet 113, into or from which the tubular member 2 is inserted or extracted, respectively formed in upper and lower surfaces of the first housing 111. In this case, the inlet 113 and the outlet 115 may be formed in parallel with each other in the longitudinal direction of the tubular member 2 so that the tubular member 2 passes straight through the inlet 113 and the outlet 115.

Meanwhile, guide members 112 and 114 are respectively provided in the inlet 113 and the outlet 115. The guide members 112 and 114 are each provided in the form of a cylindrical member having a hole formed at a center thereof. A groove is formed in a circumferential direction in an outer peripheral surface of each of the guide members 112 and 114.

The guide members 112 and 114 are installed in the first housing 111 as rim portions of the inlet 113 and the outlet 115 are inserted into the grooves of the guide members 112 and 114, respectively. One end of each of the guide members 112 and 114 has a hemispherical shape.

In this case, the guide members 112 and 114 are disposed so that the hemispherical ends thereof are directed toward the interior of the first housing 111. The guide members 112 and 114 serve to guide the movement of the tubular member 2 passing through the first housing 111.

Referring to FIG. 10, coupling holes 118 are formed in surfaces of the first and second housings 111 and 117 that face each other. That is, a second coupling hole 118*a* is formed in the first housing 111, and a second coupling hole 118*b* is formed in the second housing 117 and corresponds to the first coupling hole 118*a*.

The interiors of the first and second housings 111 and 117 may communicate with each other through the coupling holes 118. One side of a second gear 154 accommodated in the first housing 111 may protrude to the outside of the first housing 111 through the first coupling hole 118*a*. The second gear 154 will be described below.

Referring to FIGS. 10 and 12 together, a pair of guide holes 116 is symmetrically formed in the front and rear surfaces of the first housing 111 and extends in the leftward/rightward direction. Two opposite ends of a driven roller shaft 132 to be described below are inserted into the guide holes 116.

Referring back to FIGS. 9 to 12, the second housing 117 of the tubular member moving apparatus 101 according to the second embodiment of the present disclosure may accommodate and protect the actuator 140, the control unit 170, and the energy storage means 190 therein. The second housing 117 has a box-shaped structure having a rectangular parallelepiped shape, and the manipulation unit 180 to be described below is provided at a left side of the second housing 117.

The actuator 140 is installed in the second housing 117 and provides driving power for rotating the driving roller 121. For example, the actuator 140 may be an electric motor.

A driving shaft 142 may be coupled to a rear portion of the actuator 140, and the driving shaft 142 is connected to the driving roller 21 by the power transmitting member 150. In this case, the power transmitting member 150 includes a first gear 152 and the second gear 154.

The first gear 152 is coupled to the driving shaft 142. The first gear 152 may be positioned to correspond to the second coupling hole 118*b* and coupled to the second gear 154 to be described below through the second coupling hole 118*b*.

The energy storage means 190 supplies electrical energy for operating the actuator 140. In this case, the energy storage means 190 may be connected to a terminal provided in the second housing 117. Therefore, the energy storage means 190 may be charged by being supplied with electrical energy from an external power source connected to the terminal.

The control unit 170 refers to a processor capable of controlling an operation, a rotation direction, a rotational speed, and the like of the actuator 140. For example, the control unit 170 may be configured as a printed circuit board (PCB) or a micro-control unit (MCU).

The actuator 140 is electrically connected to the control unit 170 and the energy storage means 190. The control unit 170 transmits an electrical signal for controlling the actuator 140, and the energy storage means 190 provides energy for operating the actuator 140.

Meanwhile, a left surface of the first housing 111 and a right surface of the second housing 117 are coupled to each other while being in surface contact with each other. In this case, relative positions of the first housing 111 and the second housing 117 are adjusted, and the first housing 111 and the second housing 117 are coupled, such that the first coupling hole 118*a* and the second coupling hole 118*b* are connected and correspond to each other to define the single communication hole 118.

In this case, as described above, the first housing 111 and the second housing 117 are separably coupled. For example, a guide protrusion may be formed on the first housing 111, a guide groove may be formed in the second housing 117, such that the first housing 111 may be coupled to the second housing 117 in a sliding manner. In addition, the first housing 111 and the second housing 117 may be detachably coupled by a nut and a bolt.

Therefore, according to the tubular member moving apparatus 101 according to the second embodiment of the present disclosure, the operating parts and the driving parts are accommodated in the first housing 111 and the second housing 117, and the first housing 111 and the second housing 117 are separably coupled, such that the operating parts and the driving parts may be separated.

Therefore, according to the tubular member moving apparatus 101 according to the second embodiment of the present disclosure, only the first housing 111 and the operating parts, which are contaminated by the tubular member 2, may be separated and cleaned or repaired. Therefore, it is possible to prevent damage to the driving part that may be caused during the process of cleaning or repairing the operating part.

In addition, according to the tubular member moving apparatus 101 according to the second embodiment of the present disclosure, the first housing 111 and the operating parts may be manufactured as disposable parts or replaceably manufactured and used, and the driving parts may be used multiple times while being accommodated and protected in the second housing 117.

Figure 13:
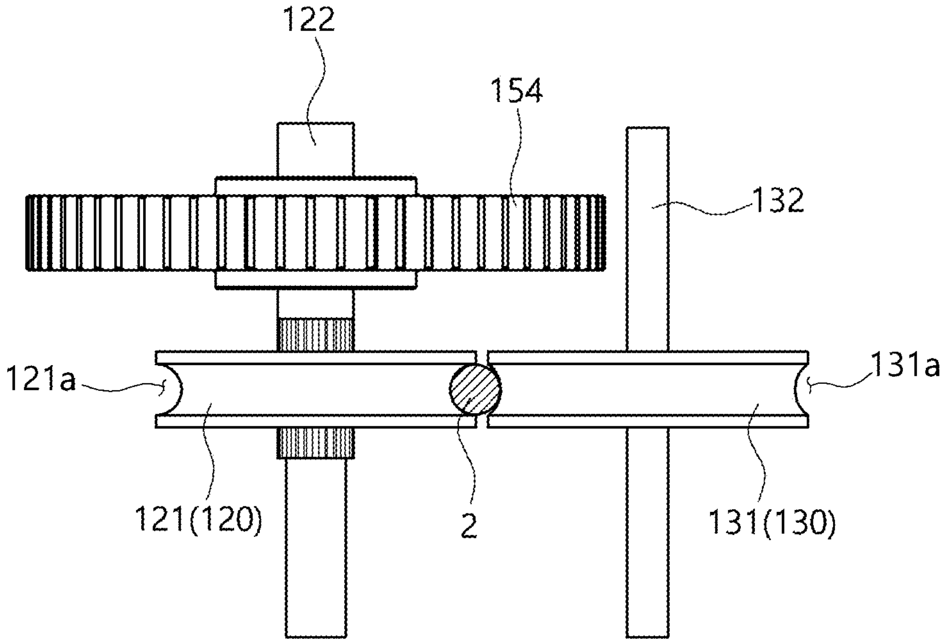
FIG. 13 is a top plan view of a driving roller, a driven roller, a rotary shaft of the driving roller, a rotary shaft of the driven roller, a first gear, and a tubular member of the tubular member moving apparatus according to the second embodiment of the present disclosure.

FIG. 13 is a top plan view of the driving roller, the driven roller, the rotary shaft of the driving roller, the rotary shaft of the driven roller, the first gear, and the tubular member of the tubular member moving apparatus according to the second embodiment of the present disclosure.

Referring to FIGS. 11 and 13, the driven roller shaft 132 and a driving roller shaft 122 are arranged in parallel in the forward/rearward direction in the first housing 111 of the tubular member moving apparatus 101 according to the second embodiment of the present disclosure. The driving roller shaft 122 is disposed at a left side in the first housing 111, and the driven roller shaft 132 is disposed at a right side of the driving roller shaft 122.

In this case, the driving roller shaft 122 and the driven roller shaft 132 are rotatably installed on the front and rear surfaces of the first housing 111. To this end, bearing members may be provided on the front and rear surfaces of the first housing 111.

In addition, as described above, the two opposite ends of the driven roller shaft 132 are coupled to the guide holes 116 of the first housing 111. Therefore, the driven roller shaft 132 may move along the guide holes 116.

The driven roller 131 is coupled to the driven roller shaft 132 so as to rotate together with the driven roller shaft 132. In addition, the driving roller 121 is coupled to the driving roller shaft 122 so as to rotate together with the driving roller shaft 122, and the second gear 154 is coaxially arranged at a rear side of the driving roller 121. In this case, the second gear 154 is positioned to correspond to the first coupling hole 118*a* so that the second gear 154 may be coupled to the first gear 152 through the first coupling hole 118*a* of the first housing 111.

The roller operating unit 160 may be provided in the first housing 111 and move the driven roller 131. In this case, the roller operating unit 160 is disposed to be more adjacent to the driven roller 131 than the driving roller 121, and the second housing 117 and the actuator 140 accommodated in the second housing 117 are disposed to be more adjacent to the driving roller 121 than the driven roller 131. That is, the roller operating unit 160 is disposed at a right side of the driven roller 131, and the second housing 117 and the actuator 140 are disposed at a left side of the driving roller 121.

Therefore, according to the tubular member moving apparatus 101 according to the second embodiment of the present disclosure, the driving roller 121 and the actuator 140 for providing driving power to the driving roller 121 are disposed to be adjacent to each other, and the driven roller 131 and the roller operating unit 160 for moving the driven roller 131 are disposed to be adjacent to each other. Therefore, it is possible to minimize a loss of driving power that may be caused during the power transmission process.

In addition, according to the tubular member moving apparatus 101 according to the second embodiment of the present disclosure, spatial efficiency in the first housing 111 may be improved, and the components may be compactly disposed, such that the tubular member moving apparatus 101 may be manufactured to be small in size.

Referring to FIGS. 10 and 11, one side of the first gear 152 is coupled to one side of the second gear 154 while penetrating the communication holes 118. The first and second gears 152 and 154 transmit driving power, which is provided by the actuator 140, to the driving roller shaft 122. The driving roller shaft 122, which receives driving power, may rotate the driving roller 121.

In this case, the power transmitting member 150 may perform a function of transmitting driving power of the actuator 140 to the driving roller 121 and a function of adjusting a rotational speed, a rotation direction, and the like of the driving roller shaft 122. To perform the functions, a plurality of other gears may be additionally disposed between the first gear 152 and the second gear 154.

The tubular member 2 is inserted into the first housing 111 through the inlet 113 of the first housing 111, passes through a portion between the driving roller 121 and the driven roller 131, and then is extracted to the outside of the first housing 111 through the outlet 115 of the first housing 111.

Referring to FIG. 13, the tubular member 2 may pass through the portion between the outer peripheral surface of the driving roller 121 and the outer peripheral surface of the driven roller 131. In this case, grooves **121*a* and 131*a* are respectively formed in the outer peripheral surface of the driving roller 121 and the outer peripheral surface of the driven roller 131 and each have a semi-circular cross-section corresponding to the outer peripheral surface of the tubular member 2**.

A left outer peripheral surface of the tubular member 2 adjoins an inner peripheral surface of the groove **121*a* of the driving roller 121, and a right outer peripheral surface of the tubular member 2 adjoins an inner peripheral surface of the groove 131*a* of the driven roller 131**.

Therefore, according to the tubular member moving apparatus 101 according to the second embodiment of the present disclosure, contact areas between the outer peripheral portion of the tubular member 2 and the outer peripheral surfaces of the driving and driven rollers 121 and 131 may increase, such that the frictional force for moving the tubular member 2 may increase.

Figure 14:
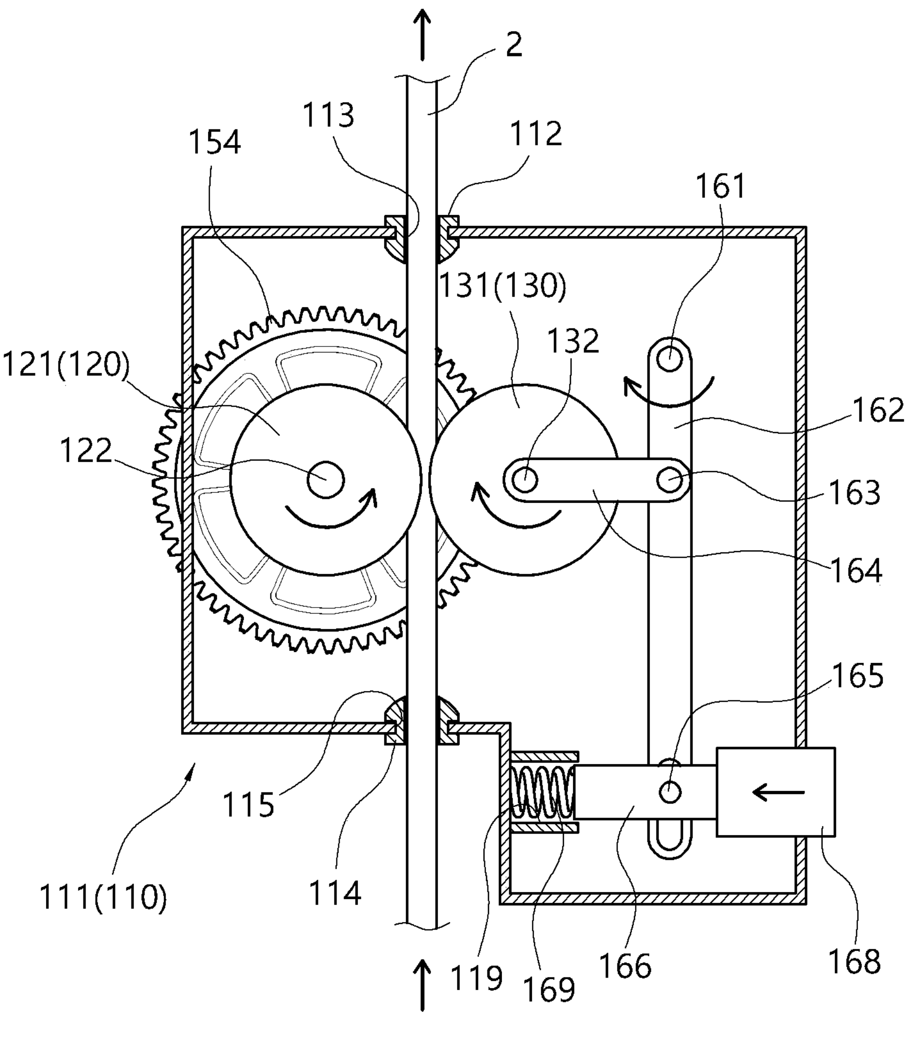
Figure 15:
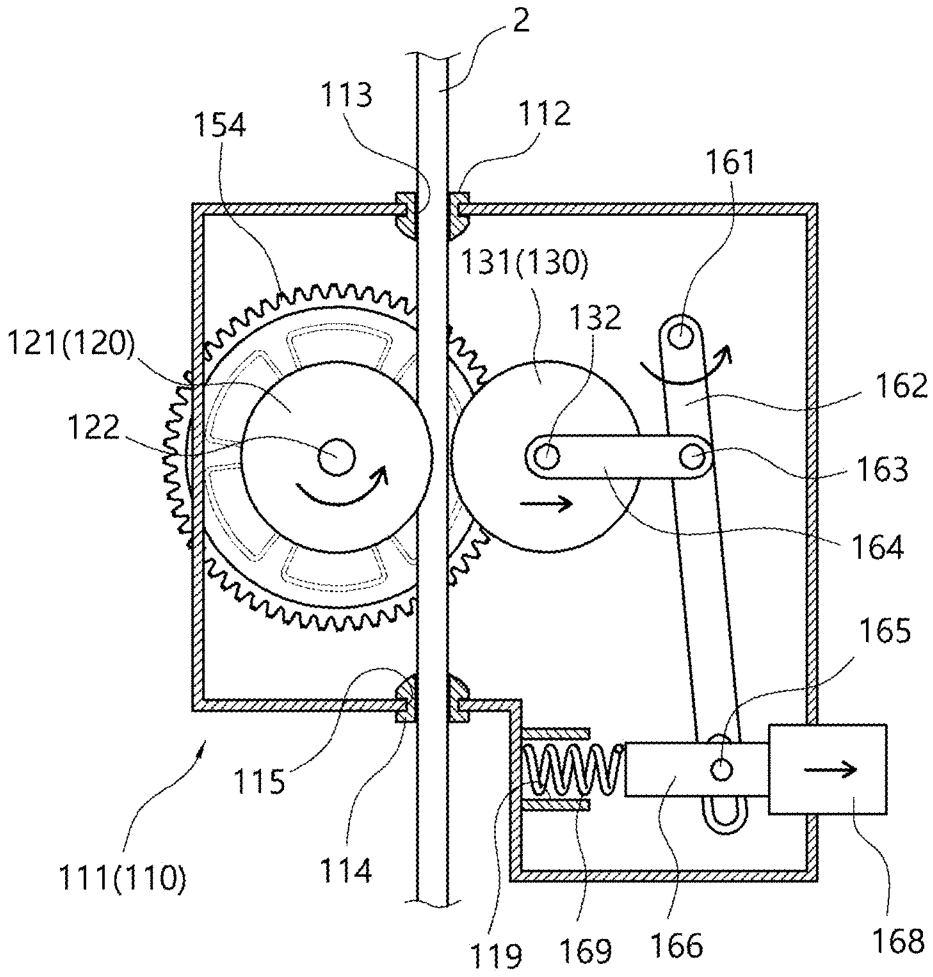

FIGS. 14 and 15 are views for explaining operating processes of the tubular member moving apparatus according to the second embodiment of the present disclosure, in which FIG. 14 is a view illustrating a state (automatic mode) in which the driven roller is positioned at the first position, and FIG. 15 is a view illustrating a state (manual mode) in which the driven roller is positioned at the second position. In this case, a cross-section of the first housing is illustrated so that the interior of the first housing is visible.

Referring to FIGS. 11, 14, and 15, in the present embodiment, the roller operating unit 160 is disposed at the right side of the driven roller 131 and accommodated in the vertical portion and the right portion of the horizontal portion of the first housing 111.

The roller operating unit 160 includes first to third links 162, 164, and 166, first to third pins 161, 163, and 165, a button member 168, and an elastic member 169.

The first link 162 is provided in the form of a rod-shaped member extending in the upward/downward direction parallel to an extension direction of the tubular member 2 passing through the first housing 111. An upper end of the first link 162 is coupled to the first housing 111 by means of the first pin 161 and configured to be pivotally rotatable about a first axis C1.

The third link 166 is coupled to a lower end of the first link 162 by means of the third pin 165. More specifically, a guide hole is provided at the lower end of the first link 162 and formed in an extension direction (upward/downward direction based on FIG. 14) of the first link 162. The lower end of the first link 162 is coupled to the third link 166 by means of the third pin 165 inserted into the guide hole of the first link 162.

Therefore, the first link 162 and the third link 166 may relatively rotate about a third axis C3 by means of the third pin 165. Meanwhile, the third link 166 is provided in the form of a rod-shaped member extending in the leftward/rightward direction.

Therefore, when the third link 166 is horizontally moved in the leftward/rightward direction, the first link 162 may be rotated about the first axis C1 by being pressed by the third link 166 and the third pin 165.

Meanwhile, the first pin 161 and the first axis C1 are spaced apart upward from a reference surface including the driving roller shaft 122 and the driven roller shaft 132. The third pin 165 and the third axis C3 are spaced apart downward from the reference surface.

The second link 164 is in the form of a rod-shaped member extending in the leftward/rightward direction. A right end of the second link 164 is coupled to the first link 162 by means of the second pin 163 and configured to be relatively rotatable about a second axis C2.

The left end of the second link 164 is coupled to the driven roller shaft 132 so as to be rotatable relative to the driven roller shaft 132. In this case, the second pin 163 and the second axis C2 are positioned between the first pin 161 and the third pin 165.

The cylindrical button member 168 is provided at a right end of the third link 166. The button member 168 is slidably coupled to the sidewall of the first housing 111, and one end of the button member 168 protrudes to the outside of the first housing 111.

The elastic member 169 is disposed at a left end of the third link 166. In this case, the elastic member may be configured as a coil spring. One side of the elastic member 169 is coupled to the left end of the third link 166, and the other side of the elastic member 169 is supported on the inner wall of the first housing 111.

In this case, an elastic member groove 119 is formed in the inner wall of the first housing 111, and the other side of the elastic member 169 may be installed in the elastic member groove 119. The elastic member groove 119 is formed to have a depth in the horizontal direction. Therefore, the force applied by the elastic member 169 to elastically press the third link 166 may be applied in the horizontal direction by the elastic member groove 119.

Referring to FIG. 14, as the button member 168 is pressed toward the inside of the first housing 111, the third link 166 is moved to the left side. As the third link 166 moves to the left side, the lower end of the first link 162 moves to the left side, and the first link 162 rotates clockwise about the first pin 161.

As the first link 162 rotates clockwise, the first link 162 pushes, to the left side, the second link 164 and the driven roller shaft 132 and the driven roller 131 connected to the second link 164.

Therefore, the driven roller 131 is positioned at the first position at which the driven roller 131 is in surface contact with the outer peripheral surface of the tubular member 2 and adjacent to the tubular member 2 and the driven roller 131 to a degree to which a frictional force is generated between the tubular member 2 and the driven roller 131. That is, two opposite portions of the outer peripheral portion of the tubular member 2 may be supported and pressed by the driving roller 121 and the driven roller 131. That is, the mode of the tubular member moving apparatus is switched to the automatic mode.

When the driving roller 121, which receives driving power from the actuator 140, rotates counterclockwise, the driven roller 131 rotates clockwise. Therefore, the tubular member 2 may move upward. When the driving roller 121 is rotated clockwise by the actuator 140, the process reverse to the above-mentioned process is performed, such that the tubular member 2 may move downward.

Meanwhile, a catching structure configured to fix the position of the button member 168 may be provided on the inner wall of the first housing 111 so that the state in which the mode is switched from the manual mode to the automatic mode may be maintained.

Therefore, when the user presses the button member 168 once by a predetermined depth in the state in which the button member 168 protrudes to the outside of the first housing 111 in the manual mode, the mode of the tubular member moving apparatus is switched to the automatic mode, and the position of the button member 168 is fixed by the catching structure. Therefore, the user may maintain the state of the manual mode of the tubular member moving apparatus without consistently applying the external force to the button member 168.

Referring to FIG. 15, in a normal state in which the external force is not applied to the button member 168 any further, the third link 166 is moved to the right side by the elastic restoring force of the elastic member 169. That is, the mode of the tubular member moving apparatus is switched from the automatic mode to the manual mode.

As the third link 166 moves to the right side, the lower end of the first link 162 moves to the right side, and the first link 162 rotates clockwise about the first pin 161.

As the first link 162 rotates clockwise, the second link 164 and the driven roller shaft 132 and the driven roller 131 connected to the second link 164 move to the right side. That is, the driven roller 131 moves to the second position at which the driven roller 131 is farther from the driving roller 121 than at the first position.

Therefore, the outer peripheral portion of the tubular member 2 is not pressed and supported by the driven roller 131 any further, such that the tubular member 2 cannot move upward even though the driving roller 121 rotates. In this case, the user may insert or extract the tubular member 2 by applying a force directly to the tubular member 2.

As described above, according to the tubular member moving apparatus 101 according to the second embodiment of the present disclosure, the button member and the roller operating unit 160 may allow the mode to be easily switched from the automatic mode in which the tubular member 2 may be automatically inserted or extracted to the manual mode in which the user may directly insert and extract the tubular member 2 or vice versa.

In addition, according to the tubular member moving apparatus 101 according to the second embodiment of the present disclosure, the roller operating unit 160 is configured as the simple link structure including the plurality of links and the plurality of pins. Therefore, it is possible to improve spatial efficiency, manufacture the tubular member moving apparatus 101 having a small size, and reducing manufacturing costs.

Meanwhile, the second pin 163 and the second axis C2 is positioned to be more adjacent to the upper end of the first link 162 than the lower end of the first link 162. Therefore, about the first axis C1, a rotation radius of the second pin 163 is smaller than a rotation radius of the third pin 165. That is, when the first link 162 rotates about the first axis C1, a movement distance of the second pin 163 in the horizontal direction is shorter than a movement distance of the third pin 165 in the horizontal direction.

That is, when the user presses the button member 168, a distance by which the button member 168 and the third link 166 move is shorter than a distance by which the driven roller 131 moves. Therefore, the user may finely adjust the movement distance of the driven roller 131 by using the button member 168.

In addition, since the second pin 163 and the second axis C2 are disposed to be more adjacent to the upper end of the first link 162 than the lower end of the first link 162, the force applied by the first link 162 to push the second link 164 to the left side may further increase as the third link 166 pushes the first link 162 to the left side in consideration of the equilibrium between the moment of force and the forces applied to the first link 162 by the first to third pins 51, 53, and 55.

Therefore, the second link 164 may apply higher force to press the driven roller shaft 132 and the driven roller 131 to the left side, and thus the driven roller 131 may apply higher force to press the tubular member 2. Therefore, the frictional forces between the tubular member 2 and the rollers 121 and 131 may increase.

Meanwhile, referring back to FIGS. 9 and 14, the manipulation unit 180 is provided at the left side of the second housing 117. The manipulation unit 180 may serve to transmit a signal to the control unit 170 to enable the control unit 170 to perform the function of generating a command signal for operating the actuator 140.

In this case, the manipulation unit 180 may be provided on a surface directed toward the outside based on the tubular member 2 passing through the first housing 111. That is, the button member 168 is provided at the right side of the first housing 111, and the manipulation unit 180 is positioned at the left side of the second housing 117.

Since the button member 168 and the manipulation unit 180 are disposed to be directed toward the outside, the user may manipulate the button member 168 and the manipulation unit 180 without interference with the tubular member 2. Therefore, the tubular member moving apparatus 101 according to the second embodiment of the present disclosure may improve convenience and efficiency related to the user's manipulation.

Hereinafter, a modified example of the tubular member moving apparatus according to the second embodiment of the present disclosure will be described. In this case, since the components in the present modified example, except for the button member, the elastic member, and the elastic member groove, may be identical to the components of the above-mentioned tubular member moving apparatus according to the second embodiment of the present disclosure, a detailed description thereof will be omitted.

Figure 16:
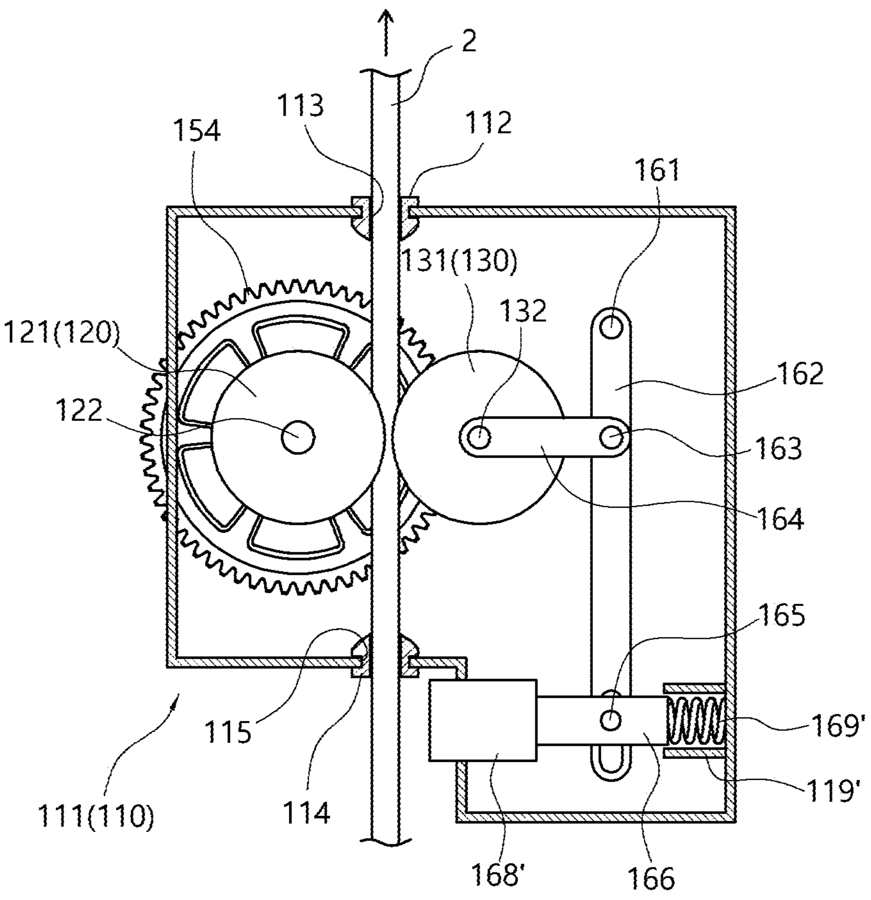
FIG. 16 is a view illustrating a modified example of the tubular member moving apparatus according to the second embodiment of the present disclosure.

FIG. 16 is a view illustrating a modified example of the tubular member moving apparatus according to the second embodiment of the present disclosure. In this case, a cross-section of the first housing is illustrated so that the interior of the first housing is visible. In this case, like reference numerals shown in the above-mentioned drawings indicate like members for performing like functions.

According to the present modified example, in the state in which no external force is applied to the tubular member moving apparatus, the elastic member presses the first link so that the driven roller moves toward the driving roller. To this end, predetermined deformation may be applied in advance to the elastic member.

Referring to FIG. 16, in the present modified example, an elastic member 169' is provided as a compressive spring and positioned at a side opposite to the driven roller 131 based on the first link 152 (at the right side based on FIG. 16). A button member 168' is positioned to face the elastic member 169' (at the left side based on FIG. 16). In this case, the button member 168' is slidably coupled to the sidewall of the first housing 111.

One side of the elastic member 169' is supported by the inner wall of the first housing 111, and the other side of the elastic member 169' is connected to the third link 166. In this case, the elastic member 169' is installed to be deformed in advance to some extent and configured to apply a predetermined elastic force to the outside so that the elastic member 169' is restored to an original shape.

Therefore, the elastic member 169' applies the elastic force in the leftward direction to the third link 166 so that the first link 162 rotates clockwise based on FIG. 16. Therefore, in the state in which no external force is applied to the tubular member moving apparatus, the driven roller 131 elastically press the tubular member 2 toward the driving roller 121.

As described above, according to the present modified example, the driven roller 131 may apply a predetermined force to press the tubular member 2 at normal times. Therefore, the tubular member 2 may move between the first driven roller 131 and the driving roller 121 regardless of a diameter of the tubular member 2.

In this case, an elastic member groove 119' is formed in the inner wall of the first housing 111, and the elastic member 169' is accommodated in the elastic member groove 119'. The elastic member groove 119' is formed to have a depth in the horizontal direction. Therefore, the force applied by the elastic member 169' to elastically press the third link 166 may be applied in the horizontal direction by the elastic member groove 119'.

Meanwhile, the user may switch the mode of the tubular member moving apparatus from the automatic mode to the manual mode by rotating the first link 162 clockwise by pressing the button member 168' toward the inside of the first housing 111.

In this case, a catching structure configured to fix the position of the button member 168' may be provided on the inner wall of the first housing 111 so that the state in which the mode is switched from the automatic mode to the manual mode may be maintained.

Therefore, when the user presses the button member 168' once by a predetermined depth in the state in which the button member 168' protrudes to the outside of the first housing 111 in the automatic mode, the mode of the tubular member moving apparatus is switched to the manual mode, and the position of the button member 168' is fixed by the catching structure. Therefore, the user may maintain the state of the manual mode of the tubular member moving apparatus without consistently applying the external force to the button member 168'.

Hereinafter, a tubular member moving apparatus according to a third embodiment of the present disclosure will be described. Because in the present embodiment, the second housing and the actuator, the power transmitting member, the control unit, and the manipulation unit provided in the second housing may be identical to those in the above-mentioned first or second embodiment of the present disclosure, a detailed description thereof will be omitted.

Figure 17:
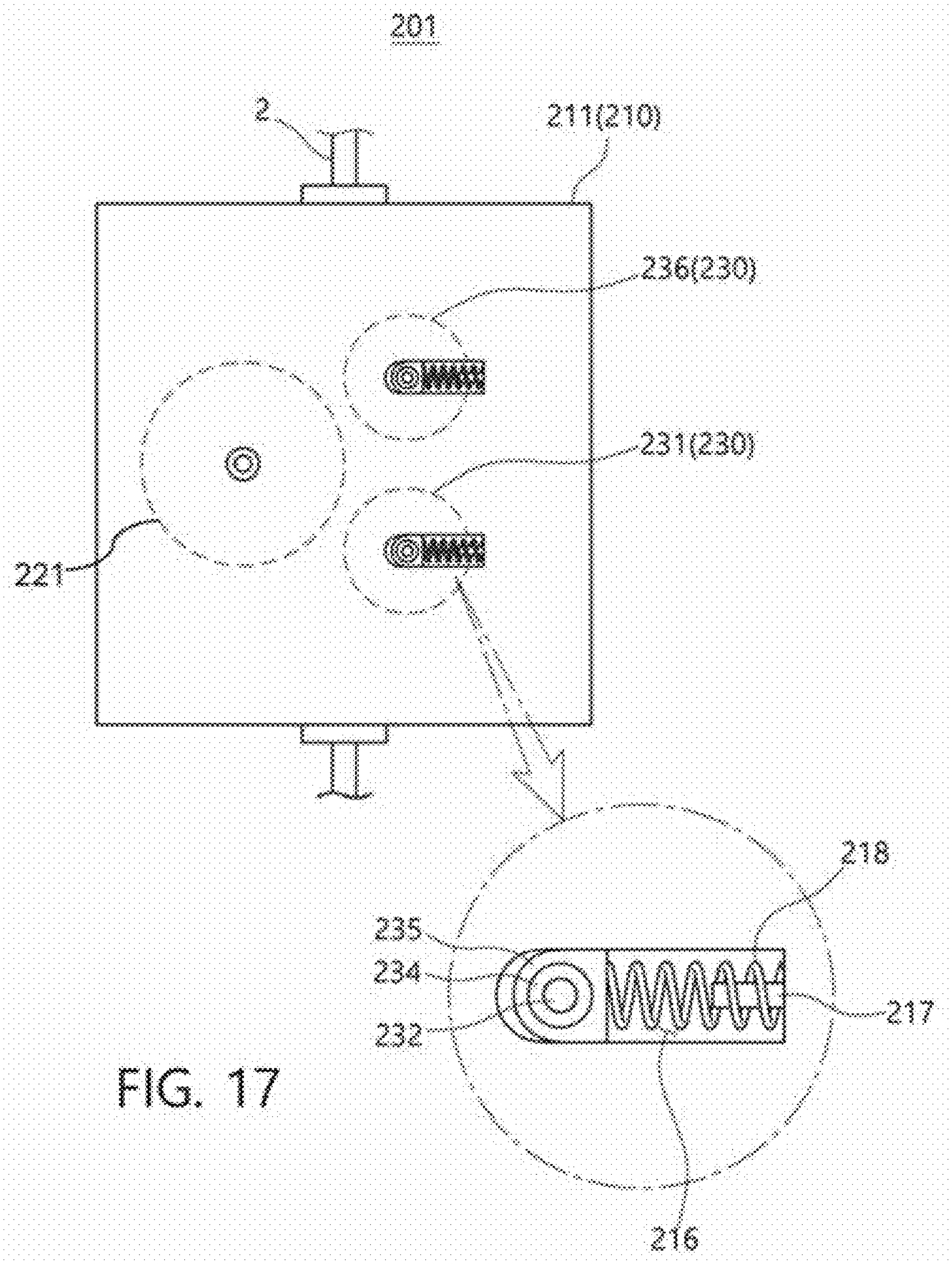
FIGS. 17 and 18 are views for explaining a tubular member moving apparatus according to a third embodiment of the present disclosure.
Figure 18:
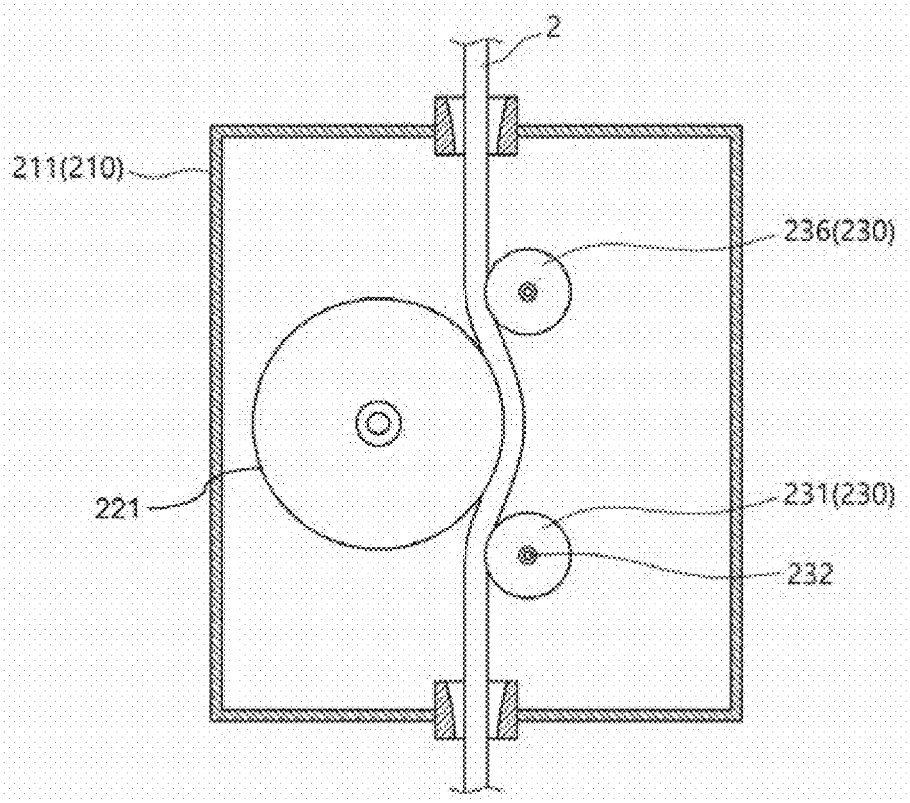

FIGS. 17 and 18 are views for explaining a tubular member moving apparatus according to a third embodiment of the present disclosure. In this case, in FIG. 17, the driving roller unit and the driven roller unit projected through the first housing are indicated by dotted lines. In FIG. 18, a cross-section of the first housing is illustrated so that the interior of the first housing is visible.

Referring to FIGS. 17 and 18, a driven roller unit 230 of a tubular member moving apparatus 201 according to a third embodiment of the present disclosure includes first and second driven rollers 231 and 236.

More specifically, the first driven roller 231 is disposed at one side of the tubular member 2, and the second driven roller 236 is spaced apart from the first driven roller 231 in the longitudinal direction of the tubular member 2. In this case, a driving roller 221 is disposed at the other side opposite to one side of the tubular member 2 and positioned between the first and second driven rollers 231 and 236.

In this case, referring to an enlarged view of FIG. 17, guide holes 216 are formed in the horizontal direction in a sidewall of a first housing 211. The sliding members 235 are provided in the guide holes 216 and configured to be slidable in the guide holes 216.

Elastic members 218 are provided in the guide holes 216 and elastically press (or elastically support) the first driven rollers 231 toward the driving roller 221. More specifically, one side of the elastic member 218 is supported by an inner wall of the guide hole 216, and the other side of the elastic member 218 is coupled to the sliding member 235. In this case, an elastic member installation portion 217 is provided on the inner wall of the guide hole 216, and the elastic member 218 may be installed on the elastic member installation portion 217.

A first driven roller shaft 232 is rotatably coupled to the sliding member 235. To this end, a bearing member 234 is provided between the sliding member 235 and the first driven roller shaft 232. The bearing member 234 may be configured as a ball bearing.

According to the present embodiment, the elastic member 218 may move the first driven roller 231 to the first position from the second position farther from the driving roller 221 than the first position until a reaction force, which acts against the elastic force of the elastic member 218, becomes equal in magnitude to the elastic force. Thereafter, the elastic member 218 elastically press (or elastically support) the first driven roller 231 toward the driving roller 221.

Therefore, according to the tubular member moving apparatus 201 according to the present embodiment, the first driven roller 231 may apply a predetermined force and press the tubular member 2 toward the driving roller 221 at normal times. In addition, the first driven roller 231 may stably press or support the tubular member 2 toward the driving roller 221 regardless of a diameter of the tubular member 2.

In addition, since the first and second driven rollers 231 and 236 press two opposite portions of the tubular member 2 based on the longitudinal direction against the driving roller 221, the tubular member 2 is bent while having a predetermined curvature along the outer peripheral surface of the driving roller 221. That is, the most parts of the tubular member 2 adjoin the outer peripheral surface of the driving roller 221.

As described above, according to the tubular member moving apparatus 201 according to the present embodiment, the contact area (or friction area) between the tubular member 2 and the driving roller 221 may increase, the tubular member 2 may more efficiently move.

Hereinafter, a modified example of the tubular member moving apparatus according to the third embodiment of the present disclosure will be described.

Figure 19:
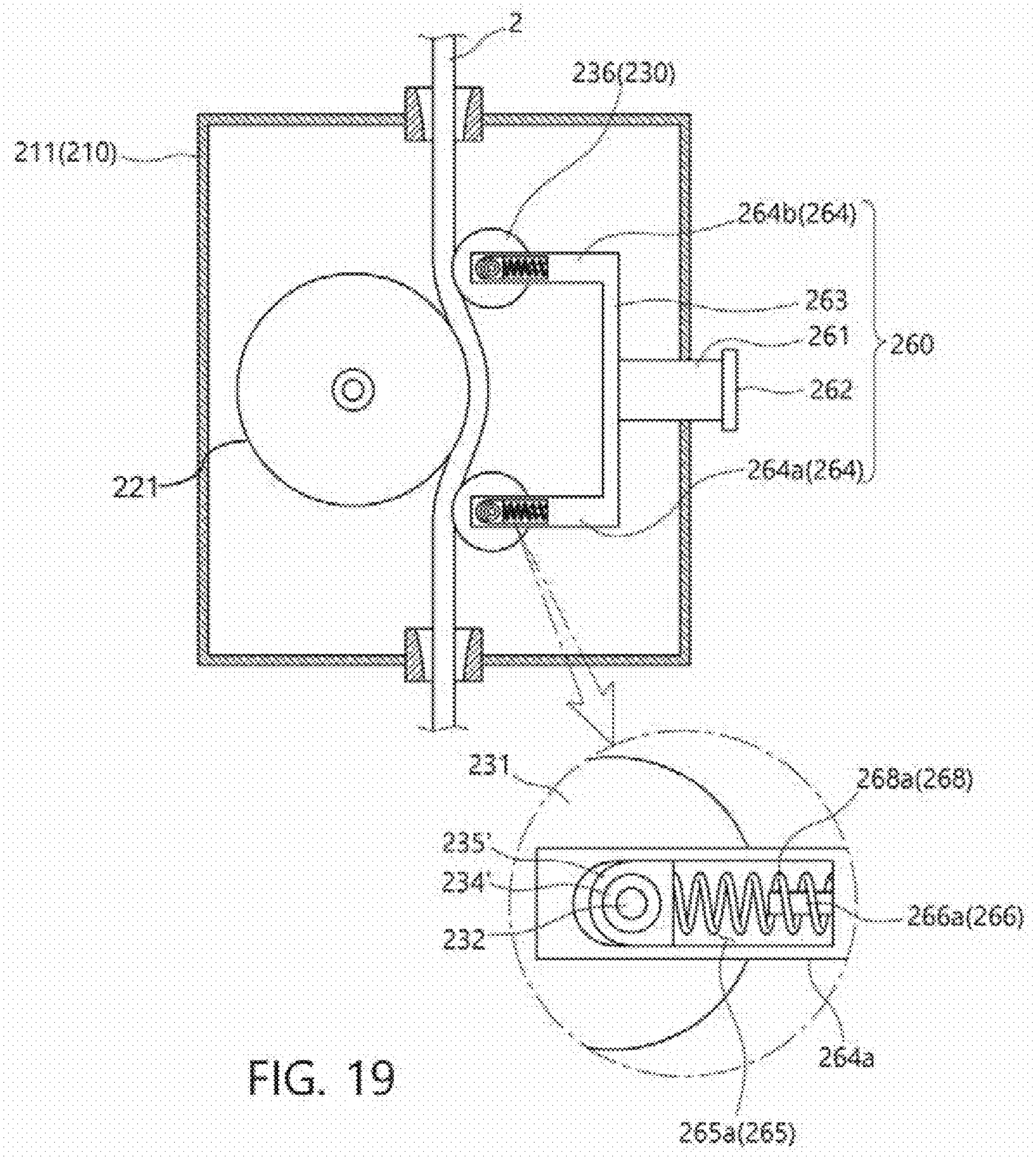
FIG. 19 is a view for explaining a modified example of the tubular member moving apparatus according to the third embodiment of the present disclosure.

FIG. 19 is a view for explaining the modified example of the tubular member moving apparatus according to the third embodiment of the present disclosure. In this case, a cross-section of the first housing is illustrated so that the interior of the first housing is visible. In this case, like reference numerals shown in the above-mentioned drawings indicate like members for performing like functions.

Referring to FIG. 19, the tubular member moving apparatus according to the present modified example further includes a roller operating unit 260 provided in the first housing 211 and configured to move the first and second driven rollers 231 and 236 to the first position from the second position farther from the driving roller 221 than the first position.

The roller operating unit 260 includes a body 261 slidably coupled to the sidewall of the first housing 211. One side of the body 261 is positioned outside the first housing 211, and the other side of the body 261 is positioned inside the first housing 211.

In this case, a manipulation member 262 is provided at one side of the body 261 to implement convenience for the user's manipulation. A connection member 263 is provided at the other side of the body 261 and branches off from the body 261 in the longitudinal direction of the tubular member 2.

The connection member 263 extends in the longitudinal direction of the tubular member 2 so that two opposite ends of the connection member 263 are positioned to correspond to the first and second driven rollers 231 and 236, respectively. A pair of coupling members 264*a* and 264*b* is respectively formed at the two opposite ends of the connection member 263 and extends toward the first and second driven rollers 231 and 236. The first and second driven rollers 231 and 236 are rotatably coupled to the coupling members 264.

Therefore, according to the tubular member moving apparatus according to the present modified example, the user may manipulate the roller manipulation unit 260 and move the driven roller unit 230 to the first position from the second position farther from the driving roller 221 than the first position. Therefore, the user may switch the mode of the tubular member moving apparatus from the automatic mode to the manual mode or vice versa.

Referring to an enlarged view of FIG. 19, guide holes 265*a* are provided in the coupling members 264*a* and formed in the movement direction of the roller operating unit 260 (the horizontal direction based on FIG. 19). A sliding member 235' is coupled inside the guide hole 265*a* and configured to be slidable along the guide hole 265*a*.

The first driven roller shaft 232 is rotatably coupled to the sliding member 235'. To this end, a bearing member 234' is provided between the first driven roller shaft 232 and the sliding member 235'. The bearing member 234' may be configured as a ball bearing.

Meanwhile, an elastic member 268*a* is provided in the guide hole 265*a* and elastically presses (or elastically supports) the first driven roller 231 toward the driving roller 221. An elastic member installation portion 266*a* is formed on an inner wall of the guide hole 265*a*, and the elastic member 268*a* may be installed on the elastic member installation portion 266*a*.

According to the present modified example, the elastic member 268 may move the driven roller unit 230 to the first position from the second position farther from the driving roller 221 than the first position until a reaction force, which acts against the elastic force, becomes equal in magnitude to the elastic force. Thereafter, the elastic member 268 elastically presses (or elastically supports) the driven roller unit 230 against the driving roller 221.

Therefore, according to the tubular member moving apparatus according to the present modified example, the driven roller unit 230 may apply a predetermined force to press the tubular member 2 toward the driving roller 221 at normal times and stably press and support the tubular member 2 toward the driving roller 221 regardless of a diameter of the tubular member 2.

In addition, since the first and second driven rollers 231 and 236 press two opposite portions of the tubular member 2 based on the longitudinal direction against the driving roller 221, the tubular member 2 is bent while having a predetermined curvature along the outer peripheral surface of the driving roller 221. That is, the most parts of the tubular member 2 adjoin the outer peripheral surface of the driving roller 221.

Therefore, according to the tubular member moving apparatus according to the present modified example, the contact area between the tubular member 2 and the driving roller 221 may increase, such that the tubular member 2 may more efficiently move.

In addition, according to the present modified example, even though an interval between the driven roller unit 230 and the driving roller 221 becomes excessively small as the roller operating unit 260 is pressed toward the interior of the first housing 211, the first and second driven rollers 231 and 236 are somewhat spaced apart from the driving roller 221 by the reaction force applied to the driven roller unit 230 by the tubular member 2, such that the interval between the driven roller unit 230 and the driving roller 221 may be adjusted somewhat.

Therefore, the tubular member moving apparatus according to the present modified example may prevent the tubular member 2 from being excessively pressed and damaged by the roller operating unit 260.

While embodiments of the present disclosure have been described above, the spirit of the present disclosure is not limited to the exemplary embodiments presented in the present specification, those skilled in the art, who understand the spirit of the present disclosure, may easily propose other embodiments by adding, changing, deleting constituent elements within the same spirit and scope of the present disclosure, and it can be said that the embodiments are also within the spirit and scope of the present disclosure.

DESCRIPTION OF REFERENCE NUMERALS

1, 101, 201: Tubular member moving apparatus
10, 110, 210: Housing
20, 120, 220: Driving roller unit
30, 130, 230: Driven roller unit
40, 42: Actuator
50, 150: Power transmitting member
60, 160, 260: Roller operating unit
70, 170: Control unit
80, 180: Manipulation unit
190: Energy storage means

What is claimed is:

1. A tubular member moving apparatus, which is configured to move a tubular member, the tubular member moving apparatus comprising:
- a first housing through which the tubular member passes;
- a driving roller unit comprising a driving roller provided in the first housing and disposed at one side of the tubular member;
- a driven roller unit comprising a first driven roller disposed at the other side of the tubular member;
- a first actuator configured to provide driving power for rotating the driving roller;
- a second housing separably coupled to the first housing and configured to accommodate the first actuator therein; and
- a roller operating unit configured to move the first driven roller to a first position from a second position farther from the driving roller than the first position adjacent to the driving roller, wherein the roller operating unit comprises:
- a first link disposed in the first housing and extending in a vertical direction parallel to a longitudinal direction of the tubular member, wherein an upper end of the first link is coupled to the first housing so as to be pivotally rotatable about a first axis;
- a second link extending in a horizontal direction perpendicular to the vertical direction, the second link having one end coupled to a middle portion of the first link so as to be relatively rotatable about a second axis and another end coupled to the first driven roller;
- a third link extending in the horizontal direction, the third link having one end coupled to a lower end of the first link so as to be relatively rotatable about a third axis; and
- a button member installed in the first housing and connected to another end of the third link, and wherein the roller operating unit is configured such that a pressing action of the button member moves the third link horizontally to push the lower end of the first link, thereby rotating the first link about the first axis and causing the second link coupled to the middle portion of the first link to move the first driven roller between the first position and the second position.

2. The tubular member moving apparatus of claim 1, wherein the roller operating unit comprises an elastic member configured to provide an elastic force so that the button member protrudes to an outside of the first housing and the first driven roller is spaced apart from the driving roller by an interval larger than a diameter of the tubular member in a state in which no external force is applied.

3. The tubular member moving apparatus of claim 1, wherein the roller operating unit comprises an elastic member configured to elastically press the first driven roller in a direction from the second position to the first position.

4. The tubular member moving apparatus of claim 1, wherein a guide member is provided in the first housing and guides the tubular member.

5. The tubular member moving apparatus of claim 1, wherein the tubular member is disposed outside the second housing while penetrating the first housing.

6. The tubular member moving apparatus of claim 1, wherein the second housing comprises an operating button configured to operate the first actuator.

7. The tubular member moving apparatus of claim 1, wherein the driven roller unit comprises a second driven roller disposed to be spaced apart from the first driven roller in a longitudinal direction of the tubular member, and the driving roller is positioned between the first and second driven rollers in the longitudinal direction of the tubular member.

8. The tubular member moving apparatus of claim 7, wherein the tubular member is moved while being bent and having a predetermined curvature along an outer peripheral surface of the driving roller in the first housing.

9. The tubular member moving apparatus of claim 7, wherein a diameter of each of the first and second driven rollers is smaller than a diameter of the driving roller.

* * * * *